(12) United States Patent
Schröder et al.

(10) Patent No.: US 9,932,612 B2
(45) Date of Patent: *Apr. 3, 2018

(54) MICROBIAL SUCCINIC ACID PRODUCERS AND PURIFICATION OF SUCCINIC ACID

(71) Applicant: BASF SE, Ludwigshafen (DE)

(72) Inventors: Hartwig Schröder, Nussloch (DE); Stefan Haefner, Speyer (DE); Gregory Von Abendroth, Mannheim (DE); Rajan Hollmann, Bad Essen (DE); Aline Raddatz, Mannheim (DE); Hansgeorg Ernst, Schweighofen (DE); Hans Gurski, Lambsheim (DE)

(73) Assignee: BASF SE, Ludwigshafen (DE)

( * ) Notice: Subject to any disclaimer, the term of this patent is extended or adjusted under 35 U.S.C. 154(b) by 309 days.

This patent is subject to a terminal disclaimer.

(21) Appl. No.: 14/676,317

(22) Filed: Apr. 1, 2015

(65) Prior Publication Data

US 2015/0197776 A1 Jul. 16, 2015

Related U.S. Application Data

(60) Continuation of application No. 14/150,206, filed on Jan. 8, 2014, now Pat. No. 9,023,632, which is a division of application No. 13/201,547, filed as application No. PCT/EP2010/051798 on Feb. 12, 2010, now Pat. No. 8,673,598.

(60) Provisional application No. 61/245,306, filed on Sep. 24, 2009.

(30) Foreign Application Priority Data

Feb. 16, 2009 (EP) .................................. 09152959
Sep. 24, 2009 (EP) .................................. 09171250

(51) Int. Cl.
*C12P 7/46* (2006.01)
*C12N 1/32* (2006.01)
*C12N 9/10* (2006.01)
*C12R 1/01* (2006.01)

(52) U.S. Cl.
CPC ............ *C12P 7/46* (2013.01); *C12N 1/32* (2013.01); *C12N 9/1029* (2013.01); *C12R 1/01* (2013.01); *C12Y 203/01054* (2013.01)

(58) Field of Classification Search
CPC . C12P 7/46; C07C 55/02; C07C 55/10; C07C 57/15; C12N 1/32; C12N 1/20; C12R 1/01; C12Y 101/02003
See application file for complete search history.

(56) References Cited

U.S. PATENT DOCUMENTS

| | | |
|---|---|---|
| 4,550,185 A | 10/1985 | Mabry et al. |
| 5,504,004 A | 4/1996 | Guettler et al. |
| 5,573,931 A | 11/1996 | Guettler et al. |
| 5,723,322 A | 3/1998 | Guettler et al. |
| 6,596,521 B1 | 7/2003 | Chang et al. |
| 7,063,968 B2 | 6/2006 | Lee et al. |
| 7,192,761 B2 | 3/2007 | Zeikus et al. |
| 7,256,016 B2 | 8/2007 | San et al. |
| 7,262,046 B2 | 8/2007 | Ka-Yiu et al. |
| 7,470,531 B2 | 12/2008 | Rehberger et al. |
| 2003/0017559 A1 | 1/2003 | Donnelly et al. |
| 2007/0042481 A1 | 2/2007 | Lee et al. |
| 2008/0293101 A1 | 11/2008 | Peters et al. |
| 2009/0137825 A1 | 5/2009 | Bauduin et al. |
| 2009/0155869 A1 | 6/2009 | Buelter et al. |
| 2010/0044626 A1 | 2/2010 | Fischer et al. |
| 2010/0159542 A1 | 6/2010 | Scholten et al. |
| 2010/0159543 A1 | 6/2010 | Scholten et al. |
| 2010/0324258 A1 | 12/2010 | Zelder et al. |
| 2011/0008851 A1 | 1/2011 | Scholten et al. |

FOREIGN PATENT DOCUMENTS

| | | |
|---|---|---|
| EP | 0805208 A1 | 11/1997 |
| EP | 1842843 A1 | 10/2007 |
| EP | 2202294 A1 | 6/2010 |
| EP | 2204443 A1 | 7/2010 |
| JP | 2007512015 A | 5/2007 |
| JP | 2008011714 A | 1/2008 |
| WO | WO-2002000846 A1 | 1/2002 |
| WO | WO-2003040690 | 5/2003 |
| WO | WO-2005052135 A1 | 6/2005 |
| WO | WO-2005116227 A1 | 12/2005 |
| WO | WO-2006034156 A2 | 3/2006 |
| WO | WO-2006066839 A2 | 6/2006 |
| WO | WO-2008013405 A1 | 1/2008 |

(Continued)

OTHER PUBLICATIONS

"Formate acetyltransferase 1", Database UniProtKB, Accession No. P09373, Feb. 8, 2011.
"Formate acetyltransferase 2", Database UniProtKB, Accession No. P32674, Feb. 8, 2011.
"IdhA D-lactate dehydrogenase [Mannheimia succiniciproducens MBEL55E (strain; MBEL55E", Database NCBI, Accession No. 3075603, May 21, 2011.
"IdhA fermentative D-lactate dehydrogenase, NAD-dependent [*Escherichia coli* str. K-12 substr. MG1655]" Database NCBI, Accession No. 946315, May 21, 2011.
"Keto-acid formate acetyltransferase", Database UniProtKB, Accession No. P42632, Feb. 8, 2011.
"Mannheimia succiniproducens MBEL55E, complete genome", EMBL database, Accession No. AE016827, Sep. 18, 2004.
"PflA pyruvate formate lyase-activating enzyme 1 [Shigella boydii CDC 3083-94]", Database NCBI, Accession No. 6268899, Jan. 14, 2011.

(Continued)

*Primary Examiner* — Kagnew H Gebreyesus
(74) *Attorney, Agent, or Firm* — Marshall, Gerstein & Borun LLP

(57) ABSTRACT

The present invention relates to bacterial strains, capable of utilizing glycerol as a carbon source for the fermentative production of succinic acid, wherein said strains are genetically modified so that they comprise a deregulation of their endogenous pyruvate-formate-lyase enzyme activity, as well as to methods of producing organic acids, in particular succinic acid, by making use of such microorganism. The present invention also relates to the downstream processing of the produced organic acids by cation exchange chromatography.

9 Claims, 2 Drawing Sheets

(56) References Cited

FOREIGN PATENT DOCUMENTS

WO  WO-2008115958 A2  9/2008
WO  WO-2009024294 A1  2/2009

OTHER PUBLICATIONS

"PflB pyruvate formate lyase I [*Escherichia coli* str. K-12 substr. MG1655]", Database NCBI, Accession No. 945514, Feb. 28, 2011.
"PflD PflD protein [Mannheimia succiniciproducens MBEL55E]", Database NCBI, Accession No. 3075405, Dec. 18, 2010.
"PflD predicted formate acetyltransferase 2 (pyruvate formate lyase II) [*Escherichia coli* str. K-12 substr. MG1655]", Database NCBI, Accession No. 948454, Feb. 28, 2011.
"PflD protein", Database UniProtKB, Accession No. Q65VK2, Nov. 30, 2010.
"Putative formate acetyltransferase", Database UniProtKB, Accession No. P75793, Feb. 8, 2011.
"Pyruvate formate lyase-activating enzyme 1 [Shigella boydii CDC 3083-94]", Database NCBI, Accession No. YP-001880903.1, Jan. 5, 2011.
"RecName: Full-Malate synthase" EMBL database, Accession No. A1JRX8, Feb. 6, 2007.
"Sub Name: Full-Isocitrate lyase", EMBL database, Accession No. A1JRX1, Feb. 6, 2007.
"TdcE pyruvate formate-lyase 4/2-ketobutyrate formate-lyase [*Escherichia coli* str. K-12 substr. MG1655)", Database NCBI, Accession No. 947623, Feb. 28, 2011.
"YbiW predicted pyruvate formate lyase [*Escherichia coli* str. K-12 substr. MG1655]", Database NCBI, Accession No. 945444, Feb. 28, 2011.
Berrios-Rivera et al., "The Effect of Increasing NADH Availability on the Redistribution of Metabolic Fluxes in *Escherichia coli* Chemostat Cultures", Metabolic Engineering, vol. 4, No. 3, pp. 230-237, 2002.
Broun et al., "Catalytic Plasticity of Fatty Acid Modification Enzymes Underlying Chemical Diversity of Plant Lipids", Science, vol. 282, pp. 1315-1317, 1998.
Chica et al, "Semi-rational approaches to engineering enzyme activity: combining the benefits of directed evolution and rational design", Current Opinion Biotechnology, vol. 16, pp. 378-384, 2005.
Devos et al., "Practical Limits of Function Prediction", Proteins: Structure, Function and Genetics, vol. 41, pp. 98-107, 2000.
Dharmadi et al., "Anaerobic Fermentation of Glycerol by *Escherichia coli*: A New Platform for Metabolic Engineering," Biotechnology and Bioengineering, vol. 94, No. 5, pp. 821-829, 2006.
Dousse et al., "Routine phenotypic identification of bacterial species of the family Pasteurellaceae isolated from animals," J. Vet. Diagn. Invest., vol. 20, pp. 716-724, 2008.
Durchschlag et al., "Large-Scale Purification and Some Properties of Malate Synthase from Baker's Yeast", Eur. J. Biochem., vol. 114, pp. 114-255, 1981.
Eggerer et al., "Uber das Katalyseprinzip der Malat-Synthase", European J. Biochem.,vol. 1, pp. 447-475, 1967.
European Opinion EP 09 17 8050, dated Feb. 23, 2010.
European Search Report EP 09 17 8048, dated Mar. 31, 2010.
European Search Report EP 09 17 8050 dated Feb. 23, 2010.
Feng et al, "Progressive Sequence Alignment as a Prerequisite to Correct Phylogenetic Trees", J. Mol. Evol., vol. 25, pp. 351-360, 1987.
Ferry, J. G., "Formate Dehydrogenase", Fems Microbiology Reviews, vol. 87, pp. 377-382,1990.
Frey, J., "Construction of a Broad Host Range Shuttle Vector for Gene Cloning and Expression in Actinobacillus pleuropneumoniae and Other Pasteurellaceae", Res. Microbial, vol. 143, pp. 263-269, 1992.
Guettler et al., "*Actinobacillus succinogenes* sp. nov., a novel succinic-acid-producing strain from the bovine rumen," Int'l J. of Systematic Bacteriol.,vol. 49, pp. 207-216, 1999.

Guo et al., "Protein tolerance to random amino acid change", PNAS, vol. 101, No. 25, pp. 9205-9210, 2004.
Higgins et al., "Fast and Sensitive Multiple Sequence Alignments on a Microcomputer", vol. 5, No. 2, pp. 151-163, 1989.
Hong et al. "The genome sequence of the capnophilic rumen bacterium Mannheimia succiniciproducens", Nature Biotechnology, vol. 22, No. 10, pp. 1275-1281, 2004.
Hong et al., "Metabolic Flux Analysis for Succinic Acid Production by Recombinant *Escherichia coli* with Amplified Malic Enzyme Activity," Biotechnology and Bioengineering, vol. 74, No. 2, pp. 89-96, 2001.
Hoyt et al. "*Escherichia coli* Isocitrate Lyase: Properties and Comparisons", Biochimica et Biophysica Acta, vol. 966, pp. 30-35,1988.
International Preliminary Report on Patentability, PCT/EP2008/006714, dated Feb. 24, 2010.
Janssen, P.H., "Characterization of a succinate-fermenting anaerobic bacterium isolated from a glycolate-degrading mixed culture", Arch. Microbial., vol. 155, pp. 288-293, 1991.
Kim et al., "Development of a Markerless Gene Knock-Out System for Mannheimia succiniciproducens Using a Temperature-Sensitive Plasmid", FEMS Microbial Lett, vol. 278, pp. 78-85, 2008.
Kimchi-Sarfaty et al. "A 'silent' polymorphism in the MDR1 gene changes substrate specificity", Science, vol. 315, pp. 525-528, 2007.
Kisselev et al., "Polypeptide release factors in prokaryotes and eukaryotes: same function, different structure", Structure,vol. 10, pp. 8-9, 2002.
Knappe et al., "A radical-chemical route to acetyl-CoA: the anaerobically induced pyruvate formate-lyase system of *Escherichia coli*," FEMS Microbiology Reviews, vol. 75, pp. 383-398, 1990.
Knappe et al., "Pyruvate formate-lyase mechanism involving the protein-based glycyl radical," Biochemical Society Transactions, vol. 21, pp. 731-734, 1993.
Kuhnert et al. , "Pasteurellaceae, Biology, Genomics, and Molecular Aspects", ISBN 978-1-904455-34-9, 2008.
Lee et al., "From Genome Sequence to Integrated Bioprocess for Succinic Acid Production by Mannheimia succiniciproducens ", Applied Microbiology Biotechnology, vol. 79, No. 1, pp. 11-22, 2008.
Lee et al., "Genome-Based Metabolic Engineering of Mannheimia succiniciproducens for Succinic Acid Production," Appl. Environ. Microbiol., vol. 72, No. 3, pp. 1939-1948, 2006.
Lee et al., "Isolation and characterization of new succinic acid-producing bacterium, Mannheimia succiniciproducens MBEL55E, from bovine rumen," Appl. Microbial. Biotechnol. vol. 58, pp. 663-668, 2002.
Lee et al., "Succinic Acid Production with Reduced By-Product Formation in the Fermentation of Anaerobiospirillum succiniciproducens Using Glycerol as a Carbon Source," Biotechnology and Bioengineering, vol. 72, No. 1, pp. 41-48, 2001.
Lee, J., "Biological conversion of lignocellulosic biomass to ethanol", J. Biotech., vol. 56, pp. 1-24, 1997.
Lee, S. Y., "BTEC 18Genome-Scale Metabolic engineering of Mannheimia Succiniciproducens for Enhanced Succinic Acid Production", Genomic and Systems Approaches to Metabolic Engineering, The 229th ACS National Meeting in San Diego, CA.,Mar. 13-17, 2005.
Leenhouts et al., "Campbell-Like Integration of Heterologous Plasmid DNA into the Chromosome of *Lactococcus lactis* subsp. lactis", Applied and Environmental Microbiology, vol. 55, pp. 394-400, 1989.
Lin et al., "Effect of Sorghum vulgare phosphoenolpyruvate carboxylase and Lactococcus lactis pyruvate carboxylase coexpression on succinate production in mutant strains of *Escherichia coli*," Appl. Microbial. Biotechnol., vol. 67, pp. 515-523, 2005.
Mackintosh et al., "Purification and Regulatory Properties of Isocitrate Lyase From *Escherichia coli* ML308", Biochem. J., vol. 250, pp. 25-31, 1988.
Maidak et al., "A new version of the RDP (Ribosomal Database Project)", Nucl. Acids Res., vol. 27, No. 1, pp. 171-173, 1999.

(56) References Cited

OTHER PUBLICATIONS

McKinlay et al., "A Genomic Perspective on the Potential of Actinobacillus succinogenes for Industrial Succinate Production," BMC Genomics, vol. 11, No. 1, p. 680, 2010.
McKinlay et al., "Insights into Actinobacillus succinogenes fermentative metabolism in a chemically defined growth medium", Appl. and Environ. Microbial.,vol. 71, pp. 6651-6656, 2005.
Muller et al., "Formate Dehydrogenase from Pseudomonas oxalaticus", Eur. J. Biochem, vol. 83, pp. 485-498, 1978.
Nackley et al. "Human catechol-o-methyltransferase haplotypes modulate protein expression by altering rRNA secondary structure", Science, vol. 314, pp. 1930-1933, 2006.
Needleman et al., "A General Method Applicable to the Search for Similarities in the Amino Acid Sequence of Two Proteins", J. Mol. Biol., vol. 48, pp. 443-453, 1970.
Nili et al., "A defined medium for rumen bacteria and identification of strains impaired in de nova biosynthesis of certain amino acids", Lett. Appl. Microbial., vol. 21, pp. 69-74, 1995.
Pascal et al., "Mutants of *Escherichia coli* K 12 with Defects in Anaerobic Pyruvate Metabolism," J. Gen. Microbial., vol. 124, pp. 35-42, 1981.
Patentability Opinion of EP Searching Authority—EP 09 178 048.6, dated Apr. 13, 2010.
Peters-Wendisch et al., "C3-Carboxylation as an anaplerotic reaction in phosphoenolpyruvate carboxylase-deficient Corynebacterium glutamicum," Arch. Microbial., vol. 165, pp. 387-396, 1996.
Rainey et al., "The genus *Nocardiopsis* represents a phylogenetically coherent taxon and a distinct actinomycete lineage: Proposal of Nocardiopsaceae fam. nov.", Int. J. Syst. Bacterial., vol. 46, pp. 1088-1092, 1996.
Redfield et al.., "Evolution of competence and DNA uptake specificity in the Pasteurellaceae", BMC Evolutionary Biology, vol. 6, No. 82, pp. 1-15, 2006.
Robertson et al., "Purification and Characterization of Isocitrate Lyase from *Escherichia coli*", Current Microbiology, vol. 14, pp. 347-350, 1987.
Saitou et al., "The neighbor-joining method: a new method for reconstructing phylogenetic trees", Mol. Biol. Evol., vol. 4, pp. 406-425, 1987.
Sanchez et al., "Novel pathway engineering design of the anaerobic central metabolic pathway in *Escherichia coli* to increase succinate yield and productivity," Metabolic Engineering, vol. 7, pp. 229-239, 2005.
Sauna et al.., "Silent polymorphisms speak: How they affect pharmacogenomics and the treatment of cancer", Cancer Research, vol. 67, No. 2, pp. 9609-9612, 2007.
Scholten et al., "Continuous Cultivation Approach for Fermentative Succinic Acid Production from Crude Glycerol by Basfia succiniciproducens DD1 ", Biotechnol Lett, vol. 31, pp. 1947-1951, 2009.
Scholten et al., "Succinic acid production by a newly isolated bacterium," Biotechnol. Lett., vol. 30, pp. 2143-2146, 2008.
Seffernick et al. "Melamine deaminase and atrazine chlorohydrolase; 98 percent identical but functionally different", J. Bacteriology, vol. 183, No. 8, pp. 2405-2410, 2001.

Sen et al. "Developments in directed evolution for improving enzyme functions", Appl. Biochem. Biotechnol., vol. 143, pp. 212-223, 2007.
Smith et al., "Identification of Common Molecular Subsequences," J. Mol. Biol.,vol. 147, pp. 195-197, 1981.
Song et al., "Development of chemically defined medium for Mannheimia succiniciproducens based on its genome sequence", Appl. Microbial. Biotechnol., vol. 79, pp. 263-272, 2008.
Song et al., "Production of succinic acid by bacterial fermentation", Enzyme and Microbial Technology, vol. 39, pp. 352-361, 2006.
Sundaram et al., "Monomeric Malate Synthase from a Thermophilic Bacillus", Archives of Biochemistry and Biophysics, vol. 199, No. 2, pp. 515-525, 1980.
Thomson et al. "The complete genome sequence and comparative genome analysis of the high pathogenicity Yersinia enterocolitica strain 8081", PLoS Genetics, vol. 2, No. 12, pp. 2039-2051, 2006.
Tishkov et al., "Catalytic Mechanism and Application of Formate Dehydrogenase", Biochemistry(Moscow), vol. 69, No. 11, pp. 1252-1267, 2004.
Varenne et al., "A Mutant of *Escherichia coli* Deficient in Pyruvate Formate Lyase," Molec. Gen. Genet.,vol. 141, pp. 181-184, 1975.
Vlysidis et al., "Experimental and Modelling Studies of the Bioconversion of Glycerol to Succinic Acid by Actinobacillus succinogenes", AIChe100 Annual Meeting, Fuels and Petrochemicals Division (202h), Nov. 18, 2008.
Watanabe et al., "Purification and Characterization of a Cold-Adapted Isocitrate Lyase and a Malate Synthase from Colwellia marls, a Psychrophilic Bacterium", Biosci. Biotechnol. Biochem., vol. 65, No. 5, pp. 1095-1103, 2001.
Whisstock et al. "Prediction of protein function from protein sequence", Q. Rev. Biophysics, vol. 36, No. 3, pp. 307-340, 2003.
White et al., "Species and size compositions and reproductive biology of rays (Chondrichthyes, Batoidea) caught in target and non-target fisheries in eastern Indonesia," J. Fish Biol., vol. 70, pp. 1809-1837, 2007.
Wishart et al. "A single mutation converts a novel phosphotyrosine binding domain into a dual-specificity phosphatase", J. Biol. Chem. ,vol. 270, No. 45, pp. 26782-26785, 1995.
Witkowski et al., "Conversion of b-ketoacyl synthase to a malonyl decarboxylase by replacement of the active cysteine with glutamine." Biochemistry,vol. 38, pp. 11643-11650, 1999.
Wu et al., "Improved Succinic Acid Production in the Anaerobic Culture of an *Escherichia coli* pflB ldhA Double Mutant as a Result of Enhanced Anaplerotic Activities in the Preceding Aerobic Culture," Applied and Environmental Microbiology, vol. 73, No. 24, pp. 7837-7843, 2007.
Yazdani et al., "Anaerobic fermentation of glycerol: a path to economic viability for the biofuels industry ," Current Opinion in Biotechnology ,vol. 18, pp. 213-219, 2007.
Zeikus et al., "Biotechnology of succinic acid production and markets for derived industrial products", Appl. Microbial. Biotechnol., vol. 51, pp. 545-552, 1999.
Zhang et al., "Fermentation of Glycerol to Succinate by Metabolically Engineered Strains of *Escherichia coli*," Applied and Environmental Microbiology, vol. 76, No. 8, pp. 2397-2401, 2010.
Zhu et al., "Effect of a single-gene knockout on the metabolic regulation in *Escherichia coli* for D-lactate production under microaerobic condition," Metab. Engineering,vol. 7, pp. 104-115, 2005.

SEQUENCE LISTING

```
<160> NUMBER OF SEQ ID NOS: 5

<210> SEQ ID NO 1
<211> LENGTH: 1517
<212> TYPE: DNA
<213> ORGANISM: Pasteurella sp.
<220> FEATURE:
<221> NAME/KEY: misc_feature
<222> LOCATION: (1)..(1517)
<223> OTHER INFORMATION: 16S rDNA

<400> SEQUENCE: 1
tttgatcctg gctcagattg aacgctggcg gcaggcttaa cacatgcaag tcgaacggta      60
gcgggaggaa agcttgcttt ctttgccgac gagtggcgga cgggtgagta atgcttgggg     120
atctggctta tggaggggga taacgacggg aaactgtcgc taataccgcg taatatcttc     180
ggattaaagg gtgggacttt cgggccaccc gccataagat gagcccaagt gggattaggt     240
agttggtggg gtaaaggcct accaagccga cgatctctag ctggtctgag aggatgacca     300
gccacactgg aactgagaca cggtccagac tcctacggga ggcagcagtg gggaatattg     360
cacaatgggg gaaccctga tgcagccatg ccgcgtgaat gaagaaggcc ttcgggttgt      420
aaagttcttt cggtgacgag gaaggtgttt gttttaatag acaagcaat tgacgttaat       480 cacagaagaa gcaccggcta actccgtgcc agcagccgcg gtaatacgga gggtgcgagc     540
gttaatcgga ataactgggc gtaaagggca tgcaggcgga cttttaagtg agatgtgaaa     600
gccccgggct taacctggga attgcatttc agactgggag tctagagtac tttagggagg     660
ggtagaattc cacgtgtagc ggtgaaatgc gtagagatgt ggaggaatac cgaaggcgaa     720
ggcagcccct tgggaagata ctgacgctca tatgcgaaag cgtggggagc aaacaggatt     780
agataccctg gtagtccacg cggtaaacgc tgtcgatttg gggattgggc tttaggcctg     840
gtgctcgtag ctaacgtgat aaatcgaccg cctggggagt acggccgcaa ggttaaaact     900
caaatgaatt gacgggggcc cgcacaagcg gtggagcatg tggtttaatt cgatgcaacg     960
cgaagaacct tacctactct tgacatccag agaatcctgt agagatacgg gagtgccttc    1020
gggagctctg agacaggtgc tgcatggctg tcgtcagctc gtgttgtgaa atgttgggtt    1080
aagtcccgca acgagcgcaa cccttatcct ttgttgccag catgtaaaga tgggaactca    1140
aaggagactg ccggtgacaa accggaggaa ggtggggatg acgtcaagtc atcatggccc    1200
ttacgagtag ggctacacac gtgctacaat ggtgcataca gagggcggcg ataccgcgag    1260
gtagagcgaa tctcagaaag tgcatcgtag tccggattgg agtctgcaac tcgactccat    1320
```

```
gaagtcggaa tcgctagtaa tcgcaaatca gaatgttgcg gtgaatacgt tcccgggcct    1380
tgtacacacc gcccgtcaca ccatgggagt gggttgtacc agaagtagat agcttaacct    1440
tcgggggggg cgtttaccac ggtatgattc atgactgggg tgaagtcgta caaggtaac    1500 cgtagggaa cctgcgg                                                    1517

<210> SEQ ID NO 2
<211> LENGTH: 3008
<212> TYPE: DNA
<213> ORGANISM: Pasteurella sp.
<220> FEATURE:
<221> NAME/KEY: misc_feature
<222> LOCATION: (1)..(3008)
<223> OTHER INFORMATION: 23S rDNA

<400> SEQUENCE: 2
agtaataacg aacgacacag gtataagaat acttgaggtt gtatggttaa gtgactaagc      60
gtacaaggtg gatgccttgg caatcagagg cgaagaagga cgtgctaatc tgcgaaaagc     120
ttgggtgagt tgataagaag cgtctaaccc aagatatccg aatgggcaa cccagtagat      180 gaagaatcta ctatcaataa ccgaatccat aggttattga ggcaaaccgg gagaactgaa     240
acatctaagt accccgagga aaagaaatca accgagatta cgtcagtagc ggcgagcgaa     300
agcgtaagag ccggcaagtg atagcatgag gattagagga atcggctggg aagccgggcg     360
gcacagggtg atagccccgt acttgaaaat cattgtgtgg tactgagctt gcgagaagta     420
gggcgggaca cgagaaatcc tgtttgaaga agggggacc atcctccaag gctaaatact      480
cctgattgac cgatagtgaa ccagtactgt gaaggaaagg cgaaaagaac cccggtgagg     540
ggagtgaaat agaacctgaa accttgtacg tacaagcagt gggagcccgc gagggtgact     600
gcgtaccttt tgtataatgg gtcagcgact tatattatgt agcgaggtta accgaatagg     660
ggagccgaag ggaaaccgag tcttaactgg gcgtcgagtt gcatgatata gacccgaaac     720
ccggtgatct agccatgggc aggttgaagg ttgggtaaca ctaactggag gaccgaaccg     780
actaatgttg aaaaattagc ggatgacctg tggctggggg tgaaaggcca atcaaaccgg     840
gagatagctg gttctccccg aaatctattt aggtagagcc ttatgtgaat accttcgggg     900
gtagagcact gtttcggcta gggggccatc ccggcttacc aacccgatgc aaactgcgaa     960
taccgaagag taatgcatag gagacacacg gcgggtgcta acgttcgtcg tggagaggga    1020
aacaacccag accgccagct aaggtcccaa agtttatatt aagtgggaaa cgaagtggga    1080
aggcttagac agctaggatg ttggcttaga agcagccatc atttaaagaa agcgtaatag    1140
ctcactagtc gagtcggcct gcgcggaaga tgtaacgggg ctcaaatata gcaccgaagc    1200
tgcggcatca ggcgtaagcc tgttgggtag gggagcgtcg tgtaagcgga agaaggtggt    1260
tcgagagggc tgctggacgt atcacgagtg cgaatgctga cataagtaac gataaaacgg    1320
gtgaaaaacc cgttcgccgg aagaccaagg gttcctgtcc aacgttaatc ggggcagggt    1380
gagtcggccc ctaaggcgag gctgaagagc gtagtcgatg ggaaacgggt taatattccc    1440
gtacttgtta taattgcgat gtggggacgg agtaggttag gttatcgacc tgttggaaaa    1500
ggtcgtttaa gttggtaggt ggagcgttta ggcaaatccg gacgcttatc aacaccgaga    1560
gatgatgacg aggcgctaag gtgccgaagt aaccgatacc acacttccag gaaaagccac    1620
taagcgtcag attataataa accgtactat aaaccgacac aggtggtcag gtagagaata    1680
ctcaggcgct tgagagaact cgggtgaagg aactaggcaa aatagcaccg taacttcggg    1740
```

```
agaaggtgcg ccggcgtaga ttgtagaggt atacccttga aggttgaacc ggtcgaagtg      1800
acccgctggc tgcaactgtt tattaaaaac acagcactct gcaaacacga aagtggacgt      1860 ataggggtgtg atgcctgccc ggtgctggaa ggttaattga tggcgttatc gcaagagaag    1920
cgcctgatcg aagccccagt aaacggcggc cgtaactata acggtcctaa ggtagcgaaa     1980
ttccttgtcg ggtaagttcc gacctgcacg aatggcataa tgatggccag gctgtctcca    2040
cccgagactc agtgaaattg aaatcgccgt gaagatgcgg tgtacccgcg gctagacgga    2100
aagaccccgt gaacctttac tatagcttga cactgaacct tgaattttga tgtgtaggat     2160
aggtgggagg ctttgaagcg gtaacgccag ttatcgtgga gccatccttg aaataccacc    2220
ctttaacgtt tgatgttcta acgaagtgcc cggaacgggt actcggacag tgtctggtgg   2280
gtagtttgac tggggcggtc tcctcccaaa gagtaacgga ggagcacgaa ggtttgctaa    2340
tgacggtcgg acatcgtcag gttagtgcaa tggtataagc aagcttaact gcgagacgga    2400
caagtcgagc aggtgcgaaa gcaggtcata gtgatccggt ggttctgaat ggaagggcca    2460
tcgctcaacg gataaaaggt actccgggga taacaggctg ataccgccca agagttcata    2520
tcgacggcgg tgtttggcac ctcgatgtcg gctcatcaca tcctggggct gaagtaggtc    2580
ccaagggtat ggctgttcgc catttaaagt ggtacgcgag ctgggtttaa aacgtcgtga    2640
gacagtttgg tccctatctg ccgtgggcgt tggagaattg agaggggctg ctcctagtac    2700
gagaggaccg gagtggacgc atcactggtg ttccggttgt gtcgccagac gcattgccgg    2760
gtagctacat gcggaagaga taagtgctga agcatctaa gcacgaaact gcctcgaga     2820 tgagttctcc cagtatttaa tactgtaagg gttgttggag acgacgacgt agataggccg    2880
ggtgtgtaag cgttgcgaga cgttgagcta accggtacta attgcccgag aggcttagcc    2940
atacaacgct caagtgtttt tggtagtgaa agttattacg gaataagtaa gtagtcaggg    3000
aatcggct                                                              3008
```

<210> SEQ ID NO 3
<211> LENGTH: 4285
<212> TYPE: DNA
<213> ORGANISM: Artificial Sequence
<220> FEATURE:
<223> OTHER INFORMATION: pSacB

<400> SEQUENCE: 3

```
tcgagaggcc tgacgtcggg cccggtacca cgcgtcatat gactagttcg gacctaggga     60
tatcgtcgac atcgatgctc ttctgcgtta attaacaatt gggatcctct agactccata   120
ggccgctttc ctggctttgc ttccagatgt atgctctcct ccggagagta ccgtgacttt   180 atttcggca caaatacagg ggtcgatgga taaatacggc gatagtttcc tgacggatga   240
tccgtatgta ccggcggaag acaagctgca aacctgtcag atggagattg atttaatggc   300
ggatgtgctg agagcaccgc cccgtgaatc cgcagaactg atccgctatg tgtttgcgga   360
tgattggccg gaataaataa agccgggctt aatacagatt aagcccgtat agggtattat   420
tactgaatac caaacagctt acggaggacg gaatgttacc cattgagaca accagactgc   480
cttctgatta ttaatatttt tcactattaa tcagaaggaa taaccatgaa ttttacccgg   540
attgacctga atacctggaa tcgcagggaa cactttgccc tttatcgtca gcagattaaa  600
tgcggattca gcctgaccac caaactcgat attaccgctt tgcgtaccgc actggcggag   660
acaggttata agttttatcc gctgatgatt tacctgatct cccgggctgt taatcagttt   720
ccggagttcc ggatggcact gaaagacaat gaacttattt actgggacca gtcagacccg   780
```

```
gtctttactg tctttcataa agaaaccgaa acattctctg cactgtcctg ccgttatttt    840
ccggatctca gtgagtttat ggcaggttat aatgcggtaa cggcagaata tcagcatgat    900
accagattgt ttccgcaggg aaatttaccg gagaatcacc tgaatatatc atcattaccg    960
tgggtgagtt ttgacgggat ttaacctgaa catcaccgga aatgatgatt attttgcccc   1020
ggttttacg atggcaaagt ttcagcagga aggtgaccgc gtattattac ctgtttctgt   1080
acaggttcat catgcagtct gtgatggctt tcatgcagca cggtttatta atacacttca   1140
gctgatgtgt gataacatac tgaaataaat taattaattc tgtatttaag ccaccgtatc   1200
cggcaggaat ggtggctttt ttttatatt ttaaccgtaa tctgtaattt cgtttcagac   1260
tggttcagga tgagctcgct tggactcctg ttgatagatc cagtaatgac ctcagaactc   1320
catctggatt tgttcagaac gctcggttgc cgccgggcgt tttttattgg tgagaatcca   1380
agcactagcg gcgcgccggc cggcccggtg tgaaataccg cacagatgcg taaggagaaa   1440
ataccgcatc aggcgctctt ccgcttcctc gctcactgac tcgctgcgct cggtcgttcg   1500
gctgcggcga gcggtatcag ctcactcaaa ggcggtaata cggttatcca cagaatcagg   1560
ggataacgca ggaaagaaca tgtgagcaaa aggccagcaa aaggccagga accgtaaaaa   1620
ggccgcgttg ctggcgtttt tccataggct ccgccccct gacgagcatc acaaaaatcg   1680
acgctcaagt cagaggtggc gaaacccgac aggactataa agataccagg cgtttccccc   1740
tggaagctcc ctcgtgcgct ctcctgttcc gaccctgccg cttaccggat acctgtccgc   1800
ctttctccct tcgggaagcg tggcgctttc tcatagctca cgctgtaggt atctcagttc   1860
ggtgtaggtc gttcgctcca agctgggctg tgtgcacgaa ccccccgttc agcccgaccg   1920
ctgcgcctta tccggtaact atcgtcttga gtccaacccg gtaagacacg acttatcgcc   1980
actggcagca gccactggta acaggattag cagagcgagg tatgtaggcg gtgctacaga   2040
gttcttgaag tggtggccta actacggcta cactagaagg acagtatttg gtatctgcgc   2100
tctgctgaag ccagttacct tcggaaaaag agttggtagc tcttgatccg gcaaacaaac   2160
caccgctggt agcggtggtt ttttgtttg caagcagcag attacgcgca gaaaaaaagg   2220
atctcaagaa gatcctttga tcttttctac ggggtctgac gctcagtgga acgaaaactc   2280
acgttaaggg attttggtca tgagattatc aaaaaggatc ttcacctaga tccttttaaa   2340
ggccggccgc ggccgccatc ggcatttct tttgcgtttt tatttgttaa ctgttaattg   2400
tccttgttca aggatgctgt ctttgacaac agatgttttc ttgcctttga tgttcagcag   2460
gaagctcggc gcaaacgttg attgtttgtc tgcgtagaat cctctgtttg tcatatagct   2520
tgtaatcacg acattgtttc ctttcgcttg aggtacagcg aagtgtgagt aagtaaaggt   2580
tacatcgtta ggatcaagat ccatttttaa cacaaggcca gttttgttca gcggcttgta   2640
tgggccagtt aaagaattag aaacataacc aagcatgtaa atatcgttag acgtaatgcc   2700
gtcaatcgtc attttgatc cgcgggagtc agtgaacagg taccatttgc cgttcatttt   2760
aaagacgttc gcgcgttcaa tttcatctgt tactgtgtta gatgcaatca gcggtttcat   2820
cacttttttc agtgtgtaat catcgtttag ctcaatcata ccgagagcgc cgtttgctaa   2880
ctcagccgtg cgttttttat cgctttgcag aagttttga ctttcttgac ggaagaatga   2940
tgtgcttttg ccatagtatg ctttgttaaa taaagattct tcgccttggt agccatcttc   3000
agttccagtg tttgcttcaa atactaagta tttgtggcct ttatcttcta cgtagtgagg   3060
atctctcagc gtatggttgt cgcctgagct gtagttgcct tcatcgatga actgctgtac   3120
```

-continued

```
attttgatac gttttccgt caccgtcaaa gattgattta taatcctcta caccgttgat    3180
gttcaaagag ctgtctgatg ctgatacgtt aacttgtgca gttgtcagtg tttgtttgcc    3240
gtaatgttta ccggagaaat cagtgtagaa taaacggatt tttccgtcag atgtaaatgt    3300
ggctgaacct gaccattctt gtgtttggtc ttttaggata gaatcatttg catcgaattt    3360
gtcgctgtct ttaaagacgc ggccagcgtt tttccagctg tcaatagaag tttcgccgac    3420
tttttgatag aacatgtaaa tcgatgtgtc atccgcattt ttaggatctc cggctaatgc    3480
aaagacgatg tggtagccgt gatagtttgc gacagtgccg tcagcgtttt gtaatggcca    3540
gctgtcccaa acgtccaggc cttttgcaga agagatattt ttaattgtgg acgaatcaaa    3600
ttcagaaact tgatattttt catttttttg ctgttcaggg atttgcagca tatcatggcg    3660
tgtaatatgg gaaatgccgt atgtttcctt atatggcttt tggttcgttt ctttcgcaaa    3720
cgcttgagtt gcgcctcctg ccagcagtgc ggtagtaaag gttaatactg ttgcttgttt    3780
tgcaaacttt ttgatgttca tcgttcatgt ctcctttttt atgtactgtg ttagcggtct    3840
gcttcttcca gccctcctgt tgaagatgg caagttagtt acgcacaata aaaaagacc    3900 taaaatatgt aaggggtgac gccaaagtat acactttgcc ctttacacat tttaggtctt    3960
gcctgcttta tcagtaacaa acccgcgcga tttactttc gacctcattc tattagactc    4020
tcgtttggat tgcaactggt ctattttcct cttttgtttg atagaaaatc ataaaggat    4080 ttgcagacta cgggcctaaa gaactaaaaa atctatctgt ttcttttcat tctctgtatt    4140
ttttatagtt tctgttgcat gggcataaag ttgcctttttt aatcacaatt cagaaaatat    4200
cataatatct catttcacta ataatagtg aacggcaggt atatgtgatg ggttaaaaag    4260
gatcggcggc cgctcgattt aaatc                                         4285
```

<210> SEQ ID NO 4
<211> LENGTH: 7161
<212> TYPE: DNA
<213> ORGANISM: Artificial Sequence
<220> FEATURE:
<223> OTHER INFORMATION: pSacB (delta pflD)

<400> SEQUENCE: 4

```
tcgagaggcc tgacgtcggg cccggtacca cgcgtcatat gactagttcg gacctaggga    60
tgggatcgag ctcttttcct tgccgacaag gcggaagctt taggggaaat tcccgtaggt    120
gccgtattgg tggatgaacg gggcaatatc attggtgaag gctggaacct ctctattgtg    180
aactcggatc ccaccgccca tgccgaaatt attgcgttgc gtaacgccgc gcagaaaatc    240
caaaattacc gcctgctcaa taccacttta tacgtgactt tagaaccctg caccatgtgc    300
gccggcgcga ttttacacag ccgaatcaaa cgcttggtat tcggggcgtc cgattacaaa    360
accggtgcgg tgggttccag atttcatttt tttgaggatt ataaaatgaa tcatgggtt    420 gagatcacaa gcgtgtgctt ataggatcaa tgcagtcaga agttaagccg cttttttccaa    480 aagcgcaggg aacagaaaaa acaacaaaaa gctaccgcac ttttacaaca cccccggctt    540
aactcctctg aaaaatagtg acaaaaaaac cgtcataatg tttacgacgg ttttttttatt    600 tcttctaata tgtcacatta agcccgtagc ctgcaagcaa ccccttaaca tgctccatta    660
attcttttgt cggcggtttt acatcttcaa gctcgtattt atcgccgagt acttcccatt    720
tatgggcgcc tagacggtga taggtaata attccacttt ttcgatattc ttcatatctt    780
taatgaaatt ccccagcatg tgcaaatctt cgtcactatc tgtataaccc ggcactacaa    840
catggcggat ccaggtacgc tgatttcgat ccgctaaata ttttgcgaat tcgagcactc    900
```

```
ttttattcgg cacgccaatc aggctttcgt gaacccgttc attcatttct ttcaggtcaa    960
gcaacacaag atccgtgtca tcaatcaatt catcaataat atgatcatga tgacggacga   1020
aaccgttggt atccaagcaa gtattaattc cttctttatg gcaggctctg aaccagtccc   1080
gtacaaattc cgcctgtaaa atagcttcac cgccggaagc ggtaactccg ccgcccgagg   1140
cgttcataaa atggcgatag gtcaccactt ctttcattaa ttcttcaacg gaatttctt   1200 taccgccgtg caaatcccag gtgtctctgt tatggcaata tttacaacgc attaagcagc   1260
cttgtaaaaa taaataaag cggattcccg gcccgtcaac tgtcccgcag gtttcaaatg   1320
aatgaattcg tcctaaaacc gacataatat gcccttaaat aatcaacaaa atatagcaag   1380
aagattatag caaagaattt cgttttttc agagaatagt caaatcttcg caaaaaacta   1440
ccgcactttt atccgcttta atcaggggaa ttaaaacaaa aaaattccgc ctattgaggc   1500
ggaatttatt aagcaataag acaaactctc aattttaata cttccttctt ttctagtatt   1560
gataagattg aaaccttgca aggatgacgg cggatttgcc gtcactctca cccaactaat   1620
gtggacgact ggtaaaccat tgcattagac caatgcaaac accaccaccg acgatgttac   1680
ctaaagtaac aggaattaaa tttttaatta ctaaatggta catatctaaa tttgcaaact   1740
gctcggcatt taaacccgtt gcctgccaga attccggcga tgcgaaattt gcaattacca   1800
tgcccatagg gatcataaac atatttgcta cgcagtgttc aaagcctgaa gcgacaaaya   1860
acccgatcgg caggatcata ataaaagctt tatccgttag agtyttgccg gcataggcca   1920
tccaaacggc aatacatacc ataatgttgc aaagaatacc taaacagaag gcttcaaycc   1980
aggtatgttc tattttatgt tgtgccgtat ttaaaatggt taatccccac tgaccgtttg   2040
ccgccatgat ctgaccggaa aaccaaatta atgcaacaat aaataaaccg ccgacaaaat   2100
taccgaarta aaccacaatc cagttacgta acatctgaat tgttgtaatt ttactctcaa   2160
agcgggcaat agtcgataaa gttgatgaag taaatagttc acagccgcaa accgccacca   2220
taattacccc gagagagaac accaaaccgc cgaccagttt agttaatccc caaggcgctc   2280
ccgcagaggc tgtttgagtt gttgtataaa aaacgaatgc aagagcaata acataccgg   2340 cagagatcgc cgataaaaat gaataggctt gttttttcgt agctttataa acgccgacgt   2400
ctaacccggt ttgagccatc tcggttggcg aagccatcca agccaattta aaatcttccg   2460
atttcattga gctttcctta gtaataaaac tactcggaaa tgagtagaac tgccttaaag   2520
cataaatgat agattaaaaa atccaaaatt gttgaatatt atttaacggg gggattataa   2580
aagattcata aattagataa tagctaattt gagtgatcca tatcacctt tacagatttt   2640 ttgacctaaa tcaaaattac ccaaatagag taataatacc attataaagg gtgtggattt   2700
attcctttgg tttacgagat aaattgctat ttaagctgat ttctgataaa aagtgcggta   2760
gatttttccc aaaaataagg aaacacaaaa tggcagaaga aacaatttc agtaaaatta   2820 ttcgtaaaga aattcccgcc gacattatat atcaagacga tcttgtcacc gcatttcgcg   2880
atattgcgcc gcaggcaaaa actcatattt taattattcc gaataaattg attccgacag   2940
taaacgacgt aaccgcccat cgtcgacatc gatgctcttc tgcgttaatt aacaattggg   3000
atcctctaga ctttgcttcc agatgtatgc tctcctccgg agagtaccgt gactttattt   3060
tcggcacaaa tacaggggtc gatggataaa tacggcgata gtttcctgac ggatgatccg   3120
tatgtaccgg cggaagacaa gctgcaaacc tgtcagatgg agattgattt aatggcggat   3180
gtgctgagag caccgccccg tgaatccgca gaactgatcc gctatgtgtt tgcggatgat   3240
```

```
tggccggaat aaataaagcc gggcttaata cagattaagc ccgtataggg tattattact    3300
gaataccaaa cagcttacgg aggacggaat gttacccatt gagacaacca gactgccttc    3360
tgattattaa tattttttcac tattaatcag aaggaataac catgaattttt acccggattg   3420 acctgaatac ctggaatcgc agggaacact ttgcccttta tcgtcagcag attaaatgcg    3480
gattcagcct gaccaccaaa ctcgatatta ccgctttgcg taccgcactg gcggagacag    3540
gttataagtt ttatccgctg atgatttacc tgatctcccg ggctgttaat cagtttccgg    3600
agttccggat ggcactgaaa gacaatgaac ttatttactg ggaccagtca gacccggtct    3660
ttactgtctt tcataaagaa accgaaacat tctctgcact gtcctgccgt tattttccgg    3720
atctcagtga gtttatggca ggttataatg cggtaacggc agaatatcag catgatacca    3780
gattgtttcc gcagggaaat ttaccggaga atcacctgaa tatatcatca ttaccgtggg    3840
tgagttttga cgggatttaa cctgaacatc accggaaatg atgattattt tgccccggtt    3900
tttacgatgg caaagtttca gcaggaaggt gaccgcgtat tattacctgt ttctgtacag    3960
gttcatcatg cagtctgtga tggctttcat gcagcacggt ttattaatac acttcagctg    4020
atgtgtgata acatactgaa ataaattaat taattctgta tttaagccac cgtatccggc    4080
aggaatggtg gcttttttttt tatattttaa ccgtaatctg taatttcgtt tcagactggt    4140
tcaggatgag ctcgcttgga ctcctgttga tagatccagt aatgacctca gaactccatc    4200
tggatttgtt cagaacgctc ggttgccgcc gggcgttttt tattggtgag aatccaagca    4260
ctagcggcgc gccggccggc ccggtgtgaa ataccgcaca gatgcgtaag gagaaaatac    4320
cgcatcaggc gctcttccgc ttcctcgctc actgactcgc tgcgctcggt cgttcggctg    4380
cggcgagcgg tatcagctca ctcaaaggcg gtaatacggt tatccacaga atcaggggat    4440
aacgcaggaa agaacatgtg agcaaaaggc cagcaaaagg ccaggaaccg taaaaaggcc    4500
gcgttgctgg cgtttttcca taggctccgc cccctgacg agcatcacaa aaatcgacgc    4560
tcaagtcaga ggtggcgaaa cccgacagga ctataaagat accaggcgtt ccccctggaa    4620
agctccctcg tgcgctctcc tgttccgacc ctgccgctta ccggatacct gtccgccttt    4680
ctcccttcgg gaagcgtggc gctttctcat agctcacgct gtaggtatct cagttcggtg    4740
taggtcgttc gctccaagct gggctgtgtg cacgaacccc ccgttcagcc cgaccgctgc    4800
gccttatccg gtaactatcg tcttgagtcc aacccggtaa gacacgactt atcgccactg    4860
gcagcagcca ctggtaacag gattagcaga gcgaggtatg taggcggtgc tacagagttc    4920
ttgaagtggt ggcctaacta cggctacact agaaggacag tatttggtat ctgcgctctg    4980
ctgaagccag ttaccttcgg aaaaagagtt ggtagctctt gatccggcaa acaaaccacc    5040
gctggtagcg gtggtttttt tgtttgcaag cagcagatta cgcgcagaaa aaaggatct    5100 caagaagatc ctttgatctt ttctacgggg tctgacgctc agtggaacga aaactcacgt    5160
taagggattt tggtcatgag attatcaaaa aggatcttca cctagatcct tttaaaggcc    5220
ggccgcggcc gccatcggca ttttcttttg cgtttttatt tgttaactgt taattgtcct    5280
tgttcaagga tgctgtcttt gacaacagat gttttcttgc ctttgatgtt cagcaggaag    5340
ctcggcgcaa acgttgattg tttgtctgcg tagaatcctc tgtttgtcat atagcttgta    5400
atcacgacat tgtttccttt cgcttgaggt acagcgaagt gtgagtaagt aaaggttaca    5460
tcgttaggat caagatccat ttttaacaca aggccagttt tgttcagcgg cttgtatggg    5520
ccagttaaag aattagaaac ataaccaagc atgtaaatat cgttagacgt aatgccgtca    5580
atcgtcattt ttgatccgcg ggagtcagtg aacaggtacc atttgccgtt catttttaaag    5640
```

-continued

```
acgttcgcgc gttcaatttc atctgttact gtgttagatg caatcagcgg tttcatcact    5700
tttttcagtg tgtaatcatc gtttagctca atcataccga gagcgccgtt tgctaactca    5760
gccgtgcgtt ttttatcgct ttgcagaagt ttttgacttt cttgacggaa gaatgatgtg    5820
cttttgccat agtatgcttt gttaaataaa gattcttcgc cttggtagcc atcttcagtt    5880
ccagtgtttg cttcaaatac taagtatttg tggcctttat cttctacgta gtgaggatct    5940
ctcagcgtat ggtgtcgcc tgagctgtag ttgccttcat cgatgaactg ctgtacattt     6000
tgatacgttt ttccgtcacc gtcaaagatt gatttataat cctctacacc gttgatgttc    6060
aaagagctgt ctgatgctga tacgttaact tgtgcagttg tcagtgtttg tttgccgtaa    6120
tgtttaccgg agaaatcagt gtagaataaa cggattttc cgtcagatgt aaatgtggct     6180
gaacctgacc attcttgtgt ttggtctttt aggatagaat catttgcatc gaatttgtcg    6240
ctgtctttaa agacgcggcc agcgttttc cagctgtcaa tagaagtttc gccgactttt     6300
tgatagaaca tgtaaatcga tgtgtcatcc gcatttttag gatctccggc taatgcaaag    6360
acgatgtggt agccgtgata gtttgcgaca gtgccgtcag cgttttgtaa tggccagctg    6420
tcccaaacgt ccaggccttt tgcagaagag atattttaa ttgtggacga atcaaattca     6480
gaaacttgat attttcatt tttttgctgt tcagggattt gcagcatatc atggcgtgta     6540
atatgggaaa tgccgtatgt ttccttatat ggcttttggt tcgtttcttt cgcaaacgct    6600
tgagttgcgc ctcctgccag cagtgcggta gtaaaggtta atactgttgc ttgttttgca    6660
aacttttga tgttcatcgt tcatgtctcc tttttatgt actgtgttag cggtctgctt      6720
cttccagccc tcctgtttga agatggcaag ttagttacgc acaataaaaa aagacctaaa    6780
atatgtaagg ggtgacgcca agtatacac tttgccctt acacatttta ggtcttgcct      6840
gctttatcag taacaaaccc gcgcgattta cttttcgacc tcattctatt agactctcgt    6900
ttggattgca actggtctat tttcctcttt tgtttgatag aaaatcataa aaggatttgc    6960
agactacggg cctaaagaac taaaaaatct atctgtttct tttcattctc tgtattttt    7020
atagtttctg ttgcatgggc ataaagttgc cttttaatc acaattcaga aaatatcata    7080
atatctcatt tcactaaata atagtgaacg gcaggtatat gtgatgggtt aaaaaggatc    7140
ggcggccgct cgatttaaat c                                              7161
```

<210> SEQ ID NO 5
<211> LENGTH: 7112
<212> TYPE: DNA
<213> ORGANISM: Artificial Sequence
<220> FEATURE:
<223> OTHER INFORMATION: pSacB (delta ldh)

<400> SEQUENCE: 5

```
tcgagaggcc tgacgtcggg cccggtacca cgcgtcatat gactagttcg gacctaggga      60
tatcgtcgac atcgatgctc ttctgcgtta attacaatt gggatcctct agacccgggg     120
attccaacct gaagactggc tcggtatgac cgaacccgtc aatattccgg gaaccagcac    180
tcaatatgct aactggcggc gccgtttaac cgcaaatata gaggatattt ttgccgatac    240
ggatattcaa catctgttaa aagaggtgaa tgctattcgt aaggaataat tttgttgcga    300
acgcaatgtg attttaacgg gtgccggata tggcacccct atcaaaacga cgaatattat    360
agacctctta cgatgacgca tcttcccca gatacgcagg attagacgga tgatgttacg    420
gaatatcccg tccctgtgcg gcaacataaa ccttaatcca ttcttcctca gtgaaggaaa    480
```

```
ttcgtaacgc atccgccgcg cttttttaccc gttcaatttt accggacccc ataaccggca    540
taattttttgc cggatgcgcc aataaccagg cataagccaa tgtatctaaa cgggtttctc    600
ctttcgtttc accgatttcg agtaatgttt tttgcaccgc ccgactgttc tcatcctgat    660
tgaataaacg accgccggca agtggcgacc atgccatcgg ttgaatacgt ttttccagta    720
aaaaatccag ggtaccgtca tcaaaagcct gacgatgaag aggcgaaatc tcaatttgat    780
tagtgattaa cggctgattc acataagatt gcaacatggc gaacttagcc ggcgtatagt    840
tagataccccc gaaataacgt actttyccgg tttgataaag ttcatcaaaa gcccgcgcga    900
tttgttcggg atccgcacag ggagaaagwc ggtgaatcag caatacatct aaatagtcgc    960
attgcagttt tcaatggaa cgttgcgccg accacataat atggcggtag ctgttgtcat   1020
agtgatggga ttttatatcg ggtaattctt cattaggata caaatcccg catttggtca   1080
ccaaagtaag ctgtgcgcgc aaggatttat ccagcgccag cgcccgtccg aattccgcct   1140
cggaagtaaa agccccgtaa caagcggcat gatccagcgt atcaacgcct aattctaatc   1200
cttgcttaac gaatgtaagc aattcctgcg gcgatttccg ccagcttttt aaccgccaga   1260
atccttgaat taagcgactg aatgttaaat cgggagccag ttgaatgtgt tgcataaaac   1320
ctccaaataa attgaatcaa acagacttaa gtataaatct ttaaagaaaa agtgcggtag   1380
aaaaatatgg attttccgca taaaaaaagc gtacccgatt aggtacgcta ttaaaaatat   1440
aagcggcgct attctactct cttatggatc tcagtcaaga aaggatccgg caaccrccga   1500
acaaatggag rcgaaraaat tgaaagacg aggaaatcag cgcgttaaaa attcccgaaa   1560
acccaccgca cttttttattg gaatttgcta accttaaaag tgcggtcaaa aagttaaaaa   1620
ttttaagatt gcaattccaa cggattctta cccgctttac gcaaagcctg atgttcttta   1680
ataatcgcca taaaaggctg tccgaagcgc tgccatttga tggcgccgac accgttgatt   1740
tgcagcattt ccactttgct ggtcggctga tacaacgaca ttttcctgcaa ggtcgcgtca   1800
ctgaacacaa tataaggcgg aatgttttct ttgtcggcaa tctgtttgcg caggaaacgc   1860
aggcgggcaa ataaatcttt gtcgtagttg gttaccgcat tgcgttgcgg agcctgtacc   1920
atggtaatgg aagataatct cggcatggcc agttccaaag acacttcgcc gcgcagcacg   1980
ggacgcgcgc tttcggtgag ctgtaatctg gtccccatgc cgaaatcgct gatgatttgt   2040
tgcacaaagc ccaaatgaat cagctgacga attaccgatt gccagtattc tttgctttta   2100
tctttgccaa ttccgtagac tttcaactca tcatgttgat tttctttat tttctgattc   2160
tgcaaaccgc gcattacgcc gattacgtat tgcgtgccga aacgttgccc ggtgcgataa   2220
atggtcgaaa ggattttctg cgcgtctaat aatccgtcat atttttttcgg cggatcgagg   2280
cagatatcac agttattaca tggcgttttgg cggttttcgc cgaaataatt taacagcact   2340
aaacgacggc aggtctggct ttcggcaaat tcgccgatgg cttccagctt atgccgttta   2400
atatcccgtt gcgggctttc cggctcttcc aataaaattt tatgcaacca ggcataatcc   2460
gccggctcgt aaaacagtac cgcttccgcc ggcaggtcgt cccgcccgc gcgcccggtt   2520
tcctgataat acgcctcaat gctgcgagat aaatcaaaat gcgccacaaa acgcacatta   2580
gatttgttga tccccatacc aaaagcaatg gtcgccacca ccacttgaat attatccgt   2640
tgaaacgcct gttgcaccgc ttcccgctgc gacggctcca tgcccgcatg ataagcggct   2700
gcggaaatgc ctcttttctt cagggcttcc gcaatgcgct ccactttgct acggctgttg   2760
caatagacga taccgctttt acctttttgc gccgccacaa aattgtataa ttgctccatc   2820
ggtttgaatt tttccaccaa ggtataacga atattcgggc ggtcaaaact acctacatac   2880
```

```
aagtgcggtt cgttcaggct gacccgggat ttaaatcgct agcgggctgc taaaggaagc   2940
ggaacacgta gaaagccagt ccgcagaaac ggtgctgacc ccggatgaat gtcagctact   3000
gggctatctg gacaagggaa aacgcaagcg caaagagaaa gcaggtagct tgcagtgggc   3060
ttacatggcg atagctagac tgggcggttt tatggacagc aagcgaaccg gaattgccag   3120
ctggggcgcc ctctggtaag gttgggaagc cctgcaaagt aaactggatg gctttcttgc   3180
cgccaaggat ctgatggcgc aggggatcaa gatctgatca agagacagga tgaggatcgt   3240
ttcgcatgat tgaacaagat ggattgcacg caggttctcc ggccgcttgg gtggagaggc   3300
tattcggcta tgactgggca acagacaaa tcggctgctc tgatgccgcc gtgttccggc   3360
tgtcagcgca ggggcgcccg gttcttttg tcaagaccga cctgtccggt gccctgaatg   3420
aactgcagga cgaggcagcg cggctatcgt ggctggccac gacgggcgtt ccttgcgcag   3480
ctgtgctcga cgttgtcact gaagcgggaa gggactggct gctattgggc gaagtgccgg   3540
ggcaggatct cctgtcatct caccttgctc ctgccgagaa agtatccatc atggctgatg   3600
caatgcggcg gctgcatacg cttgatccgg ctacctgccc attcgaccac caagcgaaac   3660
atcgcatcga gcgagcacgt actcggatgg aagccggtct tgtcgatcag gatgatctgg   3720
acgaagagca tcaggggctc gcgccagccg aactgttcgc caggctcaag gcgcgcatgc   3780
ccgacggcga ggatctcgtc gtgacccatg gcgatgcctg cttgccgaat atcatggtgg   3840
aaaatggccg cttttctgga ttcatcgact gtggccggct gggtgtggcg gaccgctatc   3900
aggacatagc gttggctacc cgtgatattg ctgaagagct tggcggcgaa tgggctgacc   3960
gcttcctcgt gctttacggt atcgccgctc ccgattcgca gcgcatcgcc ttctatcgcc   4020
ttcttgacga gttcttctga gcgggactct ggggttcgaa atgaccgacc aagcgacgcc   4080
caacctgcca tcacgagatt tcgattccac cgccgccttc tatgaaaggt tgggcttcgg   4140
aatcgttttc cgggacgccg gctggatgat cctccagcgc ggggatctca tgctggagtt   4200
cttcgcccac gctagcggcg cgccggccgg cccggtgtga ataccgcac agatgcgtaa   4260 ggagaaaata ccgcatcagg cgctcttccg cttcctcgct cactgactcg ctgcgctcgg   4320
tcgttcggct gcggcgagcg gtatcagctc actcaaaggc ggtaatacgg ttatccacag   4380
aatcagggga taacgcagga aagaacatgt gagcaaaagg ccagcaaaag gccaggaacc   4440
gtaaaaaggc cgcgttgctg gcgttttttcc ataggctccg ccccctgac gagcatcaca   4500 aaaatcgacg ctcaagtcag aggtggcgaa acccgacagg actataaaga taccaggcgt   4560
ttccccctgg aagctccctc gtgcgctctc ctgttccgac cctgccgctt accggatacc   4620
tgtccgcctt tctcccttcg ggaagcgtgg cgctttctca tagctcacgc tgtaggtatc   4680
tcagttcggt gtaggtcgtt cgctccaagc tgggctgtgt gcacgaaccc cccgttcagc   4740
ccgaccgctg cgccttatcc ggtaactatc gtcttgagtc aacccggta agacacgact   4800 tatcgccact ggcagcagcc actggtaaca ggattagcag agcgaggtat gtaggcggtg   4860
ctacagagtt cttgaagtgg tggcctaact acggctacac tagaaggaca gtatttggta   4920
tctgcgctct gctgaagcca gttaccttcg gaaaaagagt tggtagctct tgatccggca   4980
aacaaaccac cgctggtagc ggtggttttt ttgtttgcaa gcagcagatt acgcgcagaa   5040
aaaaaggatc tcaagaagat cctttgatct tttctacggg gtctgacgct cagtggaacg   5100
aaaactcacg ttaagggatt ttggtcatga gattatcaaa aaggatcttc acctagatcc   5160
ttttaaaggc cggccgcggc cgccatcggc attttctttt gcgttttat ttgttaactg   5220
```

```
ttaattgtcc ttgttcaagg atgctgtctt tgacaacaga tgttttcttg cctttgatgt    5280
tcagcaggaa gctcggcgca aacgttgatt gtttgtctgc gtagaatcct ctgtttgtca    5340
tatagcttgt aatcacgaca ttgtttcctt tcgcttgagg tacagcgaag tgtgagtaag    5400
taaaggttac atcgttagga tcaagatcca tttttaacac aaggccagtt ttgttcagcg    5460
gcttgtatgg gccagttaaa gaattagaaa cataaccaag catgtaaata tcgttagacg    5520
taatgccgtc aatcgtcatt tttgatccgc gggagtcagt gaacaggtac catttgccgt    5580
tcattttaaa gacgttcgcg cgttcaattt catctgttac tgtgttagat gcaatcagcg    5640
gtttcatcac ttttttcagt gtgtaatcat cgtttagctc aatcataccg agagcgccgt    5700
ttgctaactc agccgtgcgt tttttatcgc tttgcagaag ttttttgactt tcttgacgga    5760 agaatgatgt gcttttgcca tagtatgctt tgttaaataa agattcttcg ccttggtagc    5820
catcttcagt tccagtgttt gcttcaaata ctaagtattt gtggccttta tcttctacgt    5880
agtgaggatc tctcagcgta tggttgtcgc ctgagctgta gttgccttca tcgatgaact    5940
gctgtacatt ttgatacgtt tttccgtcac cgtcaaagat tgatttataa tcctctacac    6000
cgttgatgtt caaagagctg tctgatgctg atacgttaac ttgtgcagtt gtcagtgttt    6060
gtttgccgta atgtttaccg gagaaatcag tgtagaataa acggattttt ccgtcagatg    6120
taaatgtggc tgaacctgac cattcttgtg tttggtcttt taggatagaa tcatttgcat    6180
cgaatttgtc gctgtcttta aagacgcggc cagcgttttt ccagctgtca atagaagttt    6240
cgccgacttt ttgatagaac atgtaaatcg atgtgtcatc cgcattttta ggatctccgg    6300
ctaatgcaaa gacgatgtgg tagccgtgat agtttgcgac agtgccgtca gcgttttgta    6360
atggccagct gtcccaaacg tccaggcctt ttgcagaaga gatatttta attgtggacg    6420 aatcaaattc agaaacttga tatttttcat ttttttgctg ttcagggatt tgcagcatat    6480
catggcgtgt aatatgggaa atgccgtatg tttccttata tggcttttgg ttcgtttctt    6540
tcgcaaacgc ttgagttgcg cctcctgcca gcagtgcggt agtaaaggtt aatactgttg    6600
cttgttttgc aaacttttg atgttcatcg ttcatgtctc cttttttatg tactgtgtta    6660
gcggtctgct tcttccagcc ctcctgtttg aagatggcaa gttagttacg cacaataaaa    6720
aaagacctaa aatatgtaag gggtgacgcc aaagtataca ctttgccctt tacacatttt    6780
aggtcttgcc tgctttatca gtaacaaacc cgcgcgattt acttttcgac ctcattctat    6840
tagactctcg tttggattgc aactggtcta ttttcctctt ttgtttgata gaaaatcata    6900
aaaggatttg cagactacgg gcctaaagaa ctaaaaaatc tatctgtttc ttttcattct    6960 ctgtatttt tatagtttct gttgcatggg cataaagttg ccttttaat cacaattcag    7020 aaaatatcat aatatctcat ttcactaaat aatagtgaac ggcaggtata tgtgatgggt    7080
taaaaaggat cggcggccgc tcgatttaaa tc                                  7112
```

MICROBIAL SUCCINIC ACID PRODUCERS AND PURIFICATION OF SUCCINIC ACID

RELATED APPLICATIONS

This application is a continuation of U.S. patent application Ser. No. 14/150,206, which is a divisional application of U.S. patent application Ser. No. 13/201,547 which is a national stage application (under 35 U.S.C. § 371) of PCT/EP2010/051798, filed Feb. 12, 2010, which claims benefit of European application 09152959.4, filed Feb. 16, 2009; European application 09171250.5, filed Sep. 24, 2009; and U.S. Provisional Application 61/245,306, filed Sep. 24, 2009. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is PF61823_03_Sequence_Listing. The size of the text file is 30 KB, and the text file was created on Mar. 30, 2015.

FIELD OF THE INVENTION

The present invention relates to a bacterial strain, capable of utilizing glycerol as a carbon source for the fermentative production of succinic acid, wherein said strains are genetically modified so that they comprise a deregulation of their endogenous pyruvate-formate-lyase enzyme activity as well as to methods of producing organic acids, in particular succinic acid by making use of such microorganism.

BACKGROUND OF THE INVENTION

The fermentative production of succinic acid (SA) from biomass has already drawn much attention because said acid represents an important constituent of synthetic resins or is a source of further valuable low-molecular chemical compounds, in particular tetrahydrofuran (THF), 1,4-butanediol (BDO), gamma-butyrolactone (GBL) and pyrrolidones (WO-A-2006/066839).

A SA-producing bacterium isolated from bovine rumen was described by Lee et al (2002a). The bacterium is a non-motile, non-spore-forming, mesophilic and capnophilic gram-negative rod or coccobacillus. Phylogenetic analysis based on the 16S rRNA sequence and physiological analysis indicated that the strain belongs to genus *Mannheimia* as a novel species, and has been named *Mannheimia succiniciproducens* MBEL55E. Under 100% $CO_2$ conditions, it grows well in the pH range of 6.0-7.5 and produces SA, acetic acid and formic acid at a constant ratio of 2:1:1. When *M. succiniciproducens* MBEL55E was cultured anaerobically under $CO_2$—saturation with glucose as carbon source, 19.8 g/L of glucose were consumed and 13.3 g/L of SA were produced in 7.5 h of incubation. Furthermore in this microorganism the production of SA was improved by mutation/deletion of metabolic genes. The combined mutation/deletion of the genes lactate dehydrogenase ldhA, pyruvate-formate-lyase pflB, phosphotransacetylase pta, and acetate kinase ackA genes resulted in a strain converting carbon to SA with a yield (YP/S) of 0.6 g SA per g of carbon source added. The space-time yield for the production of SA was found to be 1.8 g/liter/h. (Lee 2006)

Lin et at 2005 describe a mutant strain of *E. coli* carrying mutations in the ldh as well as in the pfl genes, described as SB202. However this strain was characterized by slow growth and the inability to ferment a saccharide to completion under anaerobic conditions. Inactive ldh and pfl did cause the carbon flux to bottle up at the pyruvate node, causing pyruvate to accumulate as the major product. In this respect the carbon yield (YP/S) of succinate on the carbon source was found to be lower than 0.15 g/g SA/Carbon.

Sanchez et al. 2005 describe *E. coli* strains carrying mutations in the ldh, the adhE, ack-pta and iclR genes. In these experiments cells were grown aerobically on complex medium, harvested, concentrated and incubated with carbon sources under anaerobic conditions. Under these specific conditions for the direct conversion of a carbohydrate to SA, carbon yields YP/S of 0.98 to 1.13 g SA per g carbon source were found, with a space-time yield of 0.79 g/l h SA. The carbon utilization for the biomass generation prior to the anaerobic conversion phase has been explicitly not included in this calculation and is not further described.

Hong and Lee (2001) describe *E. coli* strains carrying mutations in the ldh and pfl genes. These strains do produce SA from the fermentation of carbohydrate, however, with slow carbohydrate utilization and low space-time and carbon yields (YP/S) of SA from the carbohydrate carbon source glucose. In addition succinic, acetic and lactic acid were produced in a ratio of 1:0.034:1.6. In this analysis the growth of the strain carrying mutations in the ldh and pfl genes was retarded if compared to the unmutated parental strain.

Zhu et al. 2005 describe a *E. coli* strain, mutated in the pfl gene which did not produce succinic acid but lactate and showed poor growth when grown on glucose as the sole substrate.

A significant drawback of the organism *Mannheimia sucaniciproducens* is, however, its inability to metabolize glycerol, which, as a constituent of triacyl glycerols (TAGs), becomes readily available e. g. as by-product in the trans-esterification reaction of Biodiesel production (Dharmadi et al., 2006).

The fermentative production of SA from glycerol has been described in the scientific literature (Lee et al., 2001; Dharmadi et al., 2006) and with glycerol higher yields [mass of SA produced/mass of raw material consumed] than with common sugars like glucose were achieved (Lee et al., 2001). However, the space-time yield obtained with glycerol was substantially lower than with glucose (0.14 vs. 1.0 g SA/[L h]).

Only in a few cases anaerobic metabolization of glycerol to fermentation products have been described. *E. coli* is able to ferment glycerol under very specific conditions such as acidic pH, avoiding accumulation of the fermentation gas hydrogen, and appropriate medium composition (Dharmadi et al 2006, Yazdani and Gonzalez 2007). Many microorganisms are able to metabolize glycerol in the presence of external electron acceptors (respiratory metabolism), few are able to do so fermentatively (i.e. in the absence of electron acceptors). The fermentative metabolism of glycerol has been studied in great detail in several species of the Enterobacteriaceae family, such as *Citrobacter freundii* and *Klebsiella pneumoniae*. Dissimilation of glycerol in these organisms is strictly linked to their capacity to synthesize the highly reduced product 1,3-propanediol (1,3-PDO) (Dharmadi et al 2006). The conversion of glycerol into SA using *Anaerobiospirillum succiniciproducens* has been reported (Lee et al. 2001). This study demonstrated that SA could be produced with little formation of by-product acetic acid by using glycerol as a carbon source, thus facilitating purification of SA. The highest yield was obtained by intermittently feeding glycerol and yeast extract, a strategy that resulted in the production of about 19 g/L of SA. It was noted, however, that unidentified nutritional components present in yeast extract were needed for glycerol fermentation to take place. Saccharides, however, theoretically can be converted to SA with a significantly lower yield than glycerol due to the lower reduction state of saccharides compared to the polyol glycerol. The combination of saccharides with glycerol have been found to function in an SA producing anaerobic organisms (Lee et al. 2001), however without reaching SA titers beyond 29 g/l. In addition the carbon yield YP/S of was found to be only 92% and the SA/AA relation was found to be 4.9:1. Only 4 g/l glycerol were converted to succinic acid at most.

Carboxylation reactions of oxaloacetate catalyzed by the enzymes phosphoenolpyruvate carboxylase (PEPC), phosphoenolpyruvate carboxykinase (PEPCK) and pyruvate carboxylase (PycA) are utilizing $HCO_3^-$ as a source of $CO_2$ (Peters-Wendisch, P G et al 1996, 1998). Therefore hydrogencarbonate sources such as $NaHCO_3$, $KHCO_3$, $NH_4HCO_3$ and so on can be applied to fermentation and cultivation media to improve the availability of $HCO_3^-$ in the metabolization of substrates to SA. The production of SA from glucose has not been found to be dependent on the addition of $HCO_3^-$ in the prior art so far.

Biomass production by anaerobic organisms is limited by the amount of ATP produced from fermentative pathways. Biomass yield of glycerol in anaerobic organisms is lower than of saccharides, like hexoses such as glucose, fructose, pentoses such as xylose arabinose or disaccharides such as sucrose or maltose (Lee et al. 2001, Dharmadi 2007).

Earlier patent application PCT/EP2008/006714, the content of which is herewith incorporated by reference, discloses a bacterial strain, being a member of the family of Pasteurellaceae, originally isolated from rumen, and capable of utilizing glycerol as a carbon source and variant and mutant strains derived there from retaining said capability, in particular, a bacterial strain designated DD1 as deposited with DSMZ (Deutsche Sammlung von Mikroorganismen and Zellkulturen GmbH, Inhoffenstr. 7B, D-38124 Braunschweig, Germany) having the deposit number DSM 18541 (ID 06-614) and having the ability to produce succinic acid and variant or mutant strains derived there from retaining at least said ability to produce succinic acid. The DD1 strain belongs to the species *Basfia succiniciproducens* and the family of Pasteurellaceae as classified by Kuhnert et al., 2010.

There is, therefore, a need for novel bacterial strains, which have the ability to produce organic acids, in particular SA, from glycerol. In particular, such strains should produce said acids with high productivity from glycerol, especially if crude glycerol e. g. from bio diesel production can be used without prior purification. It is an object of the present invention to provide such novel strains and production processes.

SUMMARY OF THE INVENTION

The present inventors, who had isolated a bacterial strain, designated DD1, surprisingly solved said object by mutating said strain, so that the activity of the PFL protein was decreased so that said strain has the desired metabolic characteristic. Thus, they provided a new type of bacterial stain, capable of utilizing glycerol as a carbon source for the fermentative production of succinic acid, wherein said strain is genetically modified so that it comprises a deregulation of its endogenous PFL enzyme activity.

The present inventors surprisingly found that such a mutated bacterial strain, having the desired metabolic characteristic, showed largely improved technical behavior in the fermentation of SA.

Figure 1:
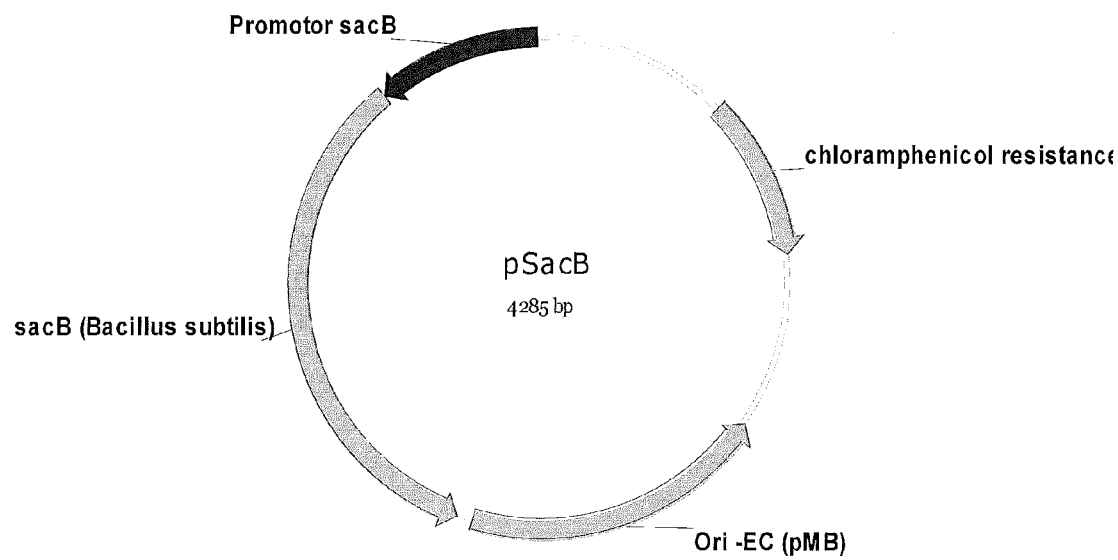
FIG. 1 depicts a schematic map of plasmid pSacB (SEQ ID NO:3).

DETAILED DESCRIPTION OF THE INVENTION a) General Definition of Particular Terms

The term "bacterial cell" as used herein refers to a prokaryotic organism, i.e. a bacterium. Bacteria can be classified based on their biochemical and microbiological properties as well as their morphology. These classification criteria are well known in the art.

The term "acid" (in the context of organic mono or dicarboxylic acids as referred to herein, i.p. acetic, lactic and SA) has to be understood in its broadest sense and also encompasses salts thereof, as for example alkali metal salts, like Na and K salts, or earth alkali salts, like Mg and Ca salts, or ammonium salts; or anhydrides of said acids.

"Identity" or "homology" between two nucleotide sequences means identity of the residues over the complete length of the aligned sequences, such as, for example, the identity calculated (for rather similar sequences) with the aid of the program needle from the bioinformatics software package EMBOSS (Version 5.0.0, webpage at emboss.sourceforge.net/what/) with the default parameters which are:

gapopen (penalty to open a gap): 10.0
gapextend (penalty to extend a gap): 0.5
datafile (scoring matrix file included in package): EDNAFUL The term "bacterial strain containing a mutated gene coding for a pyruvate-formate-lyase enzyme with decreased activity" encompasses a modified bacterial cell which has a decreased activity or even no detectable PFL activity. Methods for the detection and determination of PFL activity can be found in Knappe et al. 1990 and Knappe 1993 and references therein. Moreover, the term encompasses a bacterial cell, which has a significantly reduced PFL activity when compared to a bacterial cell exhibiting physiological pyruvate-formate-lyase activity levels. Whether a reduction is significant can be determined by statistical methods well known to those skilled in the art. Bacterial cells being deficient in PFL activity may occur naturally, i.e. due to spontaneous mutations. A bacterial cell can be modified to lack or to have significantly reduced PFL activity by various techniques. Preferably, such bacterial cells are obtainable by chemical treatment or radiation. To this end, bacterial cells will be treated by, e.g., a mutagenic chemical agent, X-rays, or UV light. In a subsequent step, those bacterial cells which lack PFL or which at least have a reduced PFL activity will be selected. Bacterial cells are also obtainable by homologous recombination techniques, which aim to mutate, disrupt or excise the PFL in the genome of the bacterial cell or introduce mutations which will lead to a mutated gene coding for a protein with decreased activity. A preferred technique for recombination, in particular for introducing mutations or for deleting sequences, is described below.

The above definition also applies to other genes coding for another enzyme mentioned herein, to be modulated, in particular, whose activity is to be deceased, diminished or switched-off.

The term "decreased activity" includes for example the expression of a gene product (e.g. pyruvate-formate-lyase (pfl), lactate dehydrogenase (ldh) or others) by said genetically manipulated (e.g., genetically engineered) microorganism at a lower level than that expressed prior to manipulation of the microorganism. Genetic manipulation can include, but is not limited to, altering or modifying regulatory sequences or sites associated with expression of a particular gene (e.g., by removing strong promoters, inducible promoters or multiple promoters), modifying the chromosomal location of a particular gene, altering nucleic acid sequences adjacent to a particular gene such as a sequence in the promoter region including regulatory sequences important for the promoter activity a ribosome binding site or transcription terminator, decreasing the copy number of a particular gene, modifying proteins (e.g., regulatory proteins, suppressors, enhancers, transcriptional activators and the like) involved in transcription of a particular gene and/or translation of a particular gene product, or any other conventional means of decreasing expression of a particular gene routine in the art (including but not limited to use of antisense nucleic acid molecules, or other methods to knock-out or block expression of the target protein).

In particular the gene can be manipulated that one or more nucleotides are being deleted from the chromosome of the host organism. The decreased activity of the gene product e.g. of a pyruvate-formate-lyase molecule, can also be obtained by introducing one or more gene mutations which lead to a decreased activity of the gene product. The decreased activity can be a reduction of the enzymatic activity by ≥50% of the non-mutated or unaltered enzyme activity, or reduction of the enzymatic activity by ≥90%, or more preferably a reduction of the enzymatic activity by ≥95%, or more preferably a reduction of the enzymatic activity by ≥98%, or even more preferably a reduction of the enzymatic activity by ≥99% or even more preferably a reduction of the enzymatic activity by ≥99.9%.

The term "recombinant" microorganism includes a microorganism (e.g., bacteria, yeast cell, fungal cell, etc.) which has been genetically altered, modified or engineered (e.g., genetically engineered) such that it exhibits an altered, modified or different genotype and/or phenotype (e.g., when the genetic modification affects coding nucleic acid sequences of the microorganism) as compared to the naturally-occurring microorganism from which it was derived. The term "promoter" refers to a DNA sequence, which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent, if the promoter is a constitutive promoter.

The term "enhancer" refers to a promoter element. An enhancer can increase the efficiency with which a particular gene is transcribed into mRNA irrespective of the distance or orientation of the enhancer relative to the start site of transcription.

The term "cloning vector" refers to a DNA molecule, such as a plasmid, cosmid, phagemid, or bacteriophage, which has the capability of replicating autonomously in a host cell and which is used to transform cells for gene manipulation. Cloning vectors typically contain one or a small number of restriction endonuclease recognition sites at which foreign DNA sequences may be inserted in a determinable fashion without loss of an essential biological function of the vector, as well as a marker gene, which is suitable for use in the identification and selection of cells transformed with the cloning vector. Marker genes typically include genes that provide tetracycline resistance or ampicillin resistance.

The term "vector" refers to a DNA molecule comprising a cloned structural gene encoding a foreign protein, which provides a gene in a recombinant host. Typically in the case of a vector destined for integration into the host genome, the cloned gene is placed or operably linked to certain upstream and downstream sequences homologous or identical t the host genetic sequence The term "recombinant host" refers to a host that may be any prokaryotic or eukaryotic cell, which contains either a cloning vector or expression vector. This term is also meant to include those prokaryotic or eukaryotic cells that have been genetically engineered to contain the cloned gene(s) in the chromosome or genome of the host cell. For examples of suitable hosts, see Sambrook et al., 1989

The terms "express," "expressing," "expressed" and "expression" refer to expression of a gene product (e.g., a biosynthetic enzyme of a gene of a pathway or reaction defined and described in this application) at a level that the resulting enzyme activity of this protein encoded for or the pathway or reaction that it refers to allows metabolic flux through this pathway or reaction in the organism in which this gene/pathway is expressed in. The expression can be done by genetic alteration of the microorganism that is used as a starting organism. In some embodiments, a microorganism can be genetically In some embodiments, a microorganism can be genetically altered (e.g., genetically engineered) to express a gene product at an increased level relative to that produced by the starting microorganism or in a comparable microorganism which has not been altered. Genetic alteration includes, but is not limited to, altering or modifying regulatory sequences or sites associated with expression of a particular gene (e.g. by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins).

A microorganism can be physically or environmentally "altered" or "modified" to express a gene product at an increased or lower level relative to level of expression of the gene product by the starting microorganism. For example, a microorganism can be treated with or cultured in the presence of an agent (chemical or genetic) known or suspected to increase or decrease the transcription and/or translation of a particular gene and/or translation of a particular gene product such that transcription and/or translation are increased or decreased. Alternatively, a microorganism can be cultured at a temperature selected to increase or decrease transcription and/or translation of a particular gene and/or translation of a particular gene product such that transcription and/or translation are increased or decreased. "Genetically modified" refers to a microorganism altered in the above sense by means of genetic engineering techniques available in the art, as for example transformation, mutation, homologous recombination.

The terms "deregulate", "deregulated" and "deregulation" refer to alteration or modification of at least one gene in a microorganism, wherein the alteration or modification results in increasing efficiency of SA in the microorganism relative to SA production in absence of the alteration or modification. In some embodiments, a gene that is altered or modified encodes an enzyme in a biosynthetic pathway or a transport protein, such that the level or activity of the biosynthetic enzyme in the microorganism is altered or modified or that the transport specificity or efficiency is altered or modified. In some embodiments, at least one gene that encodes an enzyme in a biosynthetic pathway is altered or modified such that the level or activity of the enzyme is enhanced or increased relative to the level in presence of the unaltered or wild type gene. Deregulation also includes altering the coding region of one or more genes to yield, for example, an enzyme that is feedback resistant or has a higher or lower specific activity. Also, deregulation further encompasses genetic alteration of genes encoding transcriptional factors (e.g., activators, repressors), which regulate expression of genes coding for enzymes or transport proteins. More specifically, deregulation may result in "decreased" enzyme activity, (wherein the resulting enzyme activity is less than 100% of enzyme activity as observed in the non-deregulated state is "switched-off", i.e. reversibly or irreversibly, no longer present or at least no longer detectable by a conventional analytical took a, like an enzyme activity assay.

The term "capable of utilizing" refers to the ability of a microorganism of the invention to convert a substrate, as for example glycerol into at least one structurally and/or sterically different chemical product.

An "enzyme activity involved in or associated with the fermentative conversion of glycerol to succinate" means any catalytic or regulatory activity of an enzyme which influences the conversion of glycerol into succinate and or by-products, as may be determined by anyone of the set of parameters as defined herein below.

The different yield parameters as described herein ("Yield" or YP/S; "Specific Productivity Yield"; or Space-Time-Yield (STY)) are well known in the art and are determined as described for example by Song and Lee, 2006.

"Yield" and "YP/S" (each expressed in mass of product produced/mass of material consumed) are herein used as synonyms.

The specific productivity-yield describes the amount of a product, like SA, that is produced per h and L fermentation broth per g of dry biomass. The amount of dry cell weight stated as DCW describes the quantity of biologically active microorganism in a biochemical reaction. The value is given as g product per g DCW per h (i.e. $g/gDCW^{-1} h^{-1}$).

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean an aqueous solution which is based on a fermentative process and has not been worked up or has been worked up, for example, as described herein.

b) General Definition for Different Microorganisms

The "bacterial cell" or "bacterial strain" referred to in accordance with the present invention is selected from the family of Enterobacteriaceae, Pasteurellaceae, Bacilli or Actinobacteria.

"Enterobacteriaceae" represent a large family of bacteria, including many of the more familiar bacteria, such as *Salmonella* and *Escherichia coli*. They belong to the Proteobacteria, and they are given their own order (Enterobacteriales). Members of the Enterobacteriaceae are rod-shaped. Like other Proteobacteria they have Gram-negative stains, and they are facultative anaerobes, fermenting sugars to produce lactic acid and various other end products such as succinic acid. Most also reduce nitrate to nitrite. Unlike most similar bacteria, Enterobacteriaceae generally lack cytochrome C oxidase. Most have many flagella used to move about, but a few genera are non-motile. They are non-spore forming, and mostly they are catalase-positive. Many members of this family are a normal part of the gut flora found in the intestines of humans and other animals, while others are found in water or soil, or are parasites on a variety of different animals and plants. *Escherichia coli*, better known as *E. coli*, is one of the most important model organisms, and its genetics and biochemistry have been closely studied. Most members of Enterobacteriaceae have peritrichous Type I fimbriae involved in the adhesion of the bacterial cells to their hosts. Examples for the enterobacteriaceae are *E. coli, Proteus, Salmonella, Klebsiella*, "Pasteurellaceae" comprise a large and diverse family of Gram-negative Proteobacteria with members ranging from bacteria such as *Haemophilus influenzae* to commensals of the animal and human mucosa. Most members live as commensals on mucosal surfaces of birds and mammals, especially in the upper respiratory tract. Pasteurellaceae are typically rod-shaped, and are a notable group of facultative anaerobes. They can be distinguished from the related Enterobacteriaceae by the presence of oxidase, and from most other similar bacteria by the absence of flagella. Bacteria in the family Pasteurellaceae have been classified into a number of genera based on metabolic properties and there sequences of the 16S and 23SRNA. A more precise definition of Pasteurellacea can be found in Dousse et al. 2008 and Kuhnert, P. 2008 references therein. Many of the Pasteurellaceae contain pyruvate-formate-lyase genes and are capable of anaerobically fermenting carbon sources to organic acids.

The term "Bacilli" refers to a taxonomic class of bacteria. It includes two orders, Bacillales and Lactobacillales, The *bacillus* species represents a large (~4-8×1.5 lm) cylindrical bacteria that can grow under aerobic conditions at 37° C. They are typically nonpathogenic; The genus Bacillales cotains the species Alicyclobacillaceae, Bacillaceae, Caryophanaceae, Listeriaceae, Paenibacillaceae, Planococcaceae, Sporolactobacillaceae, Staphylococcaceae, Thermoactinomycetaceae, Turicibacteraceae. Many of the Bacilli contain pyruvate-formate-lyase genes and are capable of anaerobically fermenting carbon sources to organic acids.

The term "Actinobacteria" or "Actinomycetes" refers to a group of Gram-positive bacteria with high G+C ratio. They include some of the most common soil life, playing an important role in decomposition of organic materials. Other Actinobacteria inhabit plants and animals, examples are as *Mycobacterium, Corynebacterium, Nocardia, Rhodococcus* and *Streptomyces*. Some Actinobacteria form branching filaments, which somewhat resemble the mycelia of the unrelated fungi, among which they were originally classified under the older name Actinomycetes. Most members are aerobic, but a few can grow under anaerobic conditions. Unlike the Firmicutes, the other main group of Gram-positive bacteria, they have DNA with a high GC-content.

Preferred bacterial strains are of the genus of "*Pasteurella*". The bacteria of the genus *Pasteurella* are gram-negative and facultative anaerobic. *Pasteurella* species are non-motile, pleimorphic and most often catalase- and oxidase-positive (Kuhnert and Christensen, 2008, ISBN 978-1-904455-34-9). Preferably, the bacterial cell is a *Pasteurella* bacterial cell and, more preferably, a *Pasteurella* strain DD1 cell.

Most preferably, the *Pasteurella* strain DD1 is the bacterial strain deposited under the Budapest Treaty with DSMZ (Deutsche Sammlung von Mikroorganismen und Zellkulturen, GmbH), Germany, having the deposit number DSM 18541. This strain has been originally isolated from the rumen of a cow of german origin.

*Pasteurella* bacteria can be isolated from the gastrointestinal tract of animals and, preferably, mammals. The bacterial strain DD1, in particular, can be isolated from bovine rumen and is capable of utilizing glycerol (including crude glycerol) as a carbon source. Preferably, the said strain has the ability to produce SA from glycerol (including crude glycerol), in particular, under anaerobic conditions. Moreover, the *Pasteurella* strain DD1 exhibits at least one of the following additional metabolic characteristics:
a) production of SA from sucrose; in particular, under anaerobic conditions;
b) production of succinic acid from maltose; in particular, under anaerobic conditions;
c) production of SA from D-fructose; in particular, under anaerobic conditions;
d) production of SA from D-galactose; in particular, under anaerobic conditions;
e) production of SA from D-mannose; in particular, under anaerobic conditions;
f) production of SA from D-glucose; in particular, under anaerobic conditions;
g) production of SA from D-xylose; in particular, under anaerobic conditions;
h) production of SA from L-arabinose; in particular, under anaerobic conditions;
i) no utilization of xylitol, inositol and sorbitol;
j) growth both under aerobic and anaerobic conditions;
k) growth at initial glucose concentrations of 75 g/L or more;
l) ammonia tolerance.

In particular, said strain shows at least 2, 3, 4, 5, 6, 7, 8, 9, 10, 11 or all of said metabolic characteristics.

Strain DD1 was, analyzed for the capability to co-metabolize a saccharide and the polyol glycerol (PCT/EP2008/006714). It was found that DD1 is capable to co-metabolize maltose and glycerol resulting in biomass formation, SA formation and simultaneous maltose and glycerol utilization.

c) Preferred Embodiments

A first embodiment of the invention relates to bacterial strain, capable of utilizing glycerol as a carbon source for the fermentative production of SA wherein said strain is genetically modified so that it comprises a deregulation of its endogenous pyruvate-formate-lyase enzyme activity. In particular, said pyruvate-formate-lyase enzyme activity is decreased or switched-off.

Said mutated bacterium, containing a pyruvate-formate-lyase with a decreased activity, may be constructed by genetic means as well as by inducing mutations applying methods for mutation well known in the prior art literature (examples and descriptions for the modification of bacterial genomes can be found in Saier, Milton H Jr 2008, Foster, Patricia L, 2007, Witkin, E M 1969, Eisenstark, A 1971, Walker, G C et al. 1983 and 1984, Botstein, D, and Shortle, D 1985 and references within, is capable of utilizing mixtures of different carbon sources such as saccharides and glycerol; or utilizing only glycerol. Methods to isolate strains with mutations in the pfl gene can be found in Varenne S et al. 1975. and in Pascal, M et al. 1981.

Preferably said strain has the ability to produce SA from different carbon sources (including glycerol), in particular, under anaerobic conditions.

In another embodiment of said strain, at of least one further enzyme activity involved in or associated with the fermentative conversion of glycerol to succinate is deregulated.

In particular, said strain is derived from a microorganism selected from a microorganism of the family of Enterobacteriaceae, Pasteurellaceae, Bacilli or Actinobacteria.

In particular, said strain is derived from a microorganism of the family of Pasteurellaceae, having a 16S rDNA of SEQ ID NO: 1; or a sequence, which shows a sequence homology of at least 96, 97, 98, 99 or 99.9%; and/or having a 23S rDNA of SEQ ID NO: 2; or a sequence, which shows a sequence homology of at least 95, 96, 97, 98, 99 or 99.9%. In one embodiment of the present invention the bacterial strain is derived from a microorganism of the family of Pasteurellaceae and belongs to the species *Basfia succiniciproducens*. The species *Basfia succiniciproducens* is defined by Kuhnert et al., 2010 incorporated herein by reference.

The bacterial strain of the present invention additionally shows at least one of the following additional metabolic characteristics:
a) production of succinic acid from sucrose;
b) production of succinic acid from maltose
c) production of succinic acid from maltodextrin
d) production of succinic acid from D-fructose;
e) production of succinic acid from D-galactose;
f) production of succinic acid from D-mannose;
g) production of succinic acid from D-glucose;
h) production of succinic acid from D-xylose;
i) production of succinic acid from L-arabinose;
j) production of succinic acid from lactose;
k) production of succinic acid from raffinose;
l) production of succinic acid from glycerol;
m) growth at initial glucose concentrations of 75 g/l or more
n) growth at initial glycerol concentrations of 70 g/l or more.
as for example a combination of 2, 3, 4, 5, 6, 7, 8, 9, 10, 11, 12, 13 or all of said features, with feature l) (glycerol→SA) as a mandatory constituent of each of said combinations.

In a further embodiment the strain of the invention is converting sucrose, maltose, D-fructose, D-glucose, D-xylose, L-arabinose, D-galactose, lactose, D-mannose, raffinose and/or glycerol to succinic acid with a yield coefficient YP/S of at least 0.5 g/g, preferably up to about 1.28 g/g; as for example a yield coefficient YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g, of at least 1.07 g/g, of at least 1.09 g/g of at least 1.10 g/g, of at least 1.11 g/g, of at least 1.22 g/g, or of at least 1.24 g/g In a further embodiment the strain of the invention shows at least one of the following characteristics
a) converting at least 25 g/L of glycerol to at least 25.1 g/L succinic acid, with a yield coefficient YP/S of at least 1.01 g/g;
b) converting at least one carbon source selected from sucrose, maltose, maltodextrin, D-fructose, D-glucose, D-xylose, L-arabinose, D-galactose, lactose, D-mannose, raffinose, and/or glycerol to succinic acid with a specific productivity yield of at least 0.58 g g $DCW^{-1}$ $h^{-1}$ succinic acid;
c) converting a at least one carbon source selected from sucrose, maltose, D-fructose, D-glucose, D-xylose, L-arabinose, D-galactose, lactose, D-mannose, and/or glycerol to succinic acid with a space time yield for succinic acid of at least 2.2 g/(L h) succinic acid;
d) converting at least 25 g/L of at least one carbon source selected from sucrose, maltose, D-fructose, D-glucose, D-xylose, L-arabinose, D-galactose, lactose, D-mannose, and/or glycerol to succinic acid with a space-time-yield for succinic acid of at least 2.2 g/(L h);
e) converting at least one carbon source selected from sucrose, maltose, maltodextrin, D-fructose, D-glucose, D-xylose, L-arabinose, D-galactose, lactose, D-mannose, raffinose, and/or glycerol to succinic acid with a specific productivity yield of at least 0.58 g $gDCW^{-1}$ $h^{-1}$ succinic acid and a space-time-yield for succinic acid of at least 2.2 g/(L h).

According to still another embodiment the bacterial strain of the invention is converting at least 28 g/L of glycerol to at least 28.1 g/L SA, with a yield coefficient YP/S of at least 1.0 g/g, or of >1.0 g/g, or of >1.05 g/g, or of >1.1 g/g, or of >1.15 g/g, or of >1.20 g/g, or of >1.22 g/g, or of >1.24 g/g, up to about 1.28 g/g. For example, 28 g/L of glycerol may be converted to up to about 40 or up to about 35 g/L SA.

According to still another embodiment the bacterial strain of the invention is converting at least one carbon source selected from sucrose, maltose, raffinose, maltodextrin, D-fructose, D-glucose, D-xylose, L-arabinose, D-galactose, D-mannose, and/or glycerol to SA with a specific productivity yield of at least 0.6 g g $DCW^{-1}$ $h^{-1}$ SA, or of at least of at least 0.65, of at least 0.7 g $gDCW^{-1}$ $h^{-1}$, of at least 0.75 g $gDCW^{-1}$ $h^{-1}$, or of at least 0.77 g $gDCW^{-1}$ $h^{-1}$ SA.

According to still another embodiment the bacterial strain of the invention is converting at least one carbon source selected from sucrose, maltose, raffinose, maltodextrin, D-fructose, D-glucose, D-xylose, L-arabinose, D-galactose, D-mannose, and/or glycerol to SA with a space time yield for SA of at least 2.2 g/(L h) or of at least 2.5, at least 2.75, at least 3, at least 3.25, at least 3.5 or at least 3.7 g/(L*h) SA.

According to still another embodiment the bacterial strain of the invention is converting at least 28 g/L of at least one carbon source selected from sucrose, maltose, raffinose, maltodextrin, D-fructose, D-glucose, D-xylose, L-arabinose, D-galactose, D-mannose, and/or glycerol to SA with a space-time-yield for SA of at least 2.2 g/(L h), or of at least 2.5, at least 2.75, at least 3, at least 3.25, at least 3.5 or at least 3.7 g/(L*h).

According to another embodiment the bacterial strain of the invention is converting at least one carbon source selected from sucrose, maltose, raffinose, maltodextrin, D-fructose, D-glucose, D-xylose, L-arabinose, D-galactose, D-mannose, and/or glycerol to SA with a specific productivity yield of at least 0.6 g $gDCW^{-1}$ $h^{-1}$ or of at least of at least 0.65 or of at least 0.7 g $gDCW^{-1}$ $h^{-1}$ SA, or of at least 0.77 g $gDCW^{-1}$ $h^{-1}$ SA, and a space-time-yield for SA of at least 2.2 g/(L h), or of at least 2.5, at least 2.75, at least 3, at least 3.25, at least 3.5 or at least 3.7 g/(L*h).

Preferably said strain of the invention may be derived from strain DD1 as deposited with DSMZ having the deposit number DSM 18541 or may be or derived from a variant or mutant strain of DD1 having the ability to produce succinic acid.

Particular strains of the invention are producing succinic acid (SA) and side products (SSP) in an SA/SSP proportion of >10:1, or >12.5:1, or >15:1, or >17:5.1, or >20:1, or >25:1, or >30:1, or >33:1, wherein SSP represents the sum of side products lactic acid (LA), formic acid (FA), acetic acid (AA), and malic acid (MA), each amount being expressed in g/L.

Further particular strains are producing succinic acid (SA) and the side product acetic acid (AA) in an SA/AA proportion of >10:1, or >12.5:1, or >15:1, or >17.5:1, or >20:1, or >25:1, or >30:1, or >40:1 or >50:1, or >75:1, or >90:1, each amount being expressed in g/L.

Further particular strains are producing succinic acid (SA) and the side product formic acid (FA) in an SA/FA proportion of >90:1, or >100:1, each amount being expressed in g/L.

Another embodiment of the invention relates to a process for the fermentative production of an organic acid or a salt or derivative thereof, which process comprises the steps of:
a) incubating a bacterial strain as defined in one of the preceding claims in a medium containing an assimilable carbon source and cultivating said strain under conditions favouring the formation of the desired organic acid; and
b) obtaining said organic acid, in particular SA, or salt or derivative thereof from the medium.

According to a particular process the fermentation is performed at a temperature in the range of about 10 to 60° C., as for example 20 to 50° C. 30 to 45° C. or 25 to 35° C. and at a pH of 5.0 to 9.0, as for example 5.5 to o 8, or 6 t 7, and in the presence of carbon dioxide. The pH may be controlled by the addition of $NH_4HCO_3$, $(NH_4)_2CO_3$, NaOH, $Na_2CO_3$, $NaHCO_3$, KOH, $K_2CO_3$, $KHCO_3$, $Mg(OH)_2$, $MgCO_3$, $MgH(CO_3)_2$, $Ca(OH)_2$, $CaCO_3$, $Ca(HCO_3)_2$, CaO, $CH_6N_2O_2$, $C_2H_7N$ and/or mixtures thereof.

In particular, said assimilable carbon source is selected from glycerol, sucrose, maltose, maltodextrin, D-fructose, D-galactose, D-mannose, lactose, D-glucose, D-xylose, L-arabinose, raffinose decomposition products of starch, cellulose, hemicelluloses and lignocellulose; and mixtures thereof.

In particular, said carbon source is glycerol or a mixture of glycerol and at least one further carbon source selected from sucrose, maltose, D-fructose, D-galactose, lactose, D-mannose, D-glucose, D-xylose, raffinose and L-arabinose.

According to a particular embodiment of said process, the concentration of the assimilable carbon source is adjusted to a value in a range of 5 to 80 g/l, as for example 10 to 60.

The present invention further provides a process for the fermentative production of succinic acid or a salt or derivative thereof, which process comprises the steps of:
a) incubating a bacterial strain in a medium containing at least one assimilatable carbon source and cultivating said strain under conditions favoring the formation of the desired organic acid;
b) obtaining said organic acid or salt or derivative thereof from the medium; additionally characterized by at least one of the following features:

c) conversion of at least 25 g/L of glycerol to at least 25.1 g/L succinic acid, with a yield coefficient YP/S of at least 1.0 g/g
d) conversion of at least one carbon source selected from sucrose, maltose, D-fructose, D-glucose, D-xylose, L-arabinose, D-galactose, D-mannose, raffinose, and/or glycerol to succinic acid with a specific productivity yield of at least 0.58 g gDCW$^{-1}$ h$^{-1}$ succinic acid;
e) conversion of at least one carbon source selected from sucrose, maltose, D-fructose, D-glucose, D-xylose, L-arabinose, D-galactose, lactose, D-mannose, raffinose and/or glycerol to succinic acid with a space time yield for succinic acid of at least 2.2 g/(L h) succinic acid;
f) conversion of at least 25 g/L of at least one carbon source selected from sucrose, maltose, D-fructose, D-glucose, D-xylose, L-arabinose, D-galactose, lactose, D-mannose, raffinose, and/or glycerol to succinic acid with a space-time-yield for succinic acid of at least 2.2 g/(L h);
g) conversion of at least one carbon source selected from sucrose, maltose, D-fructose, D-glucose, D-xylose, L-arabinose, D-galactose, lactose, D-mannose, raffinose, and/or glycerol to succinic acid with a specific productivity yield of at least 0.6 g gDCW$^{-1}$ h$^{-1}$ succinic acid and a space-time-yield for succinic acid of at least 2.2 g/(L h;
h) production of succinic acid (SA) and side products (SSP) in an SA/SSP proportion of >10:1, or >12.5:1, or >15:1, or >17.5:1, or >20:1, or >25:1, or >30:1, or >33:1, wherein SSP represents the sum of side products lactic acid (LA), formic acid (FA), acetic acid (AA), and malic acid (MA), each amount being expressed in g/L;
i) production of succinic acid (SA) and the side product acetic acid (AA) in an SA/AA proportion of >10:1, or >12.5:1, or >15:1, or >17.5:1, or >20:1, or >25:1, or >30:1, or >50:1, or >75:1, or >90:1, each amount being expressed in g/L.

According to a particular embodiment of said process said bacterial strain is a genetically modified strain as defined above.

The processes of the invention may be performed discontinuously or continuously. The course of the acid production may be monitored by conventional means, as for example HPLC or GC analysis.

Preferably SA is produced under anaerobic conditions. Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm.

Aerobic conditions may be established by means of conventional techniques, as for example by introducing air or oxygen at a flow rate of, for example, 0.1 to 1 or 0.2 to 0.5 vvm.

If appropriate a slight over pressure of 0.1 to 1.5 bar may be applied according to the invention.

In another embodiment the invention provides a process for the production of succinic acid and/or succinic acid ammonium salts which method comprises the fermentative production of succinic acid as defined above and additionally controlling the pH with a base ammonia or an aqueous solution thereof, or with $NH_4HCO_3$, $(NH_4)_2CO_3$, NaOH, $Na_2CO_3$, $NaHCO_3$, KOH, $K_2CO_3$, $KHCO_3$, $Mg(OH)_2$, $MgCO_3$, $MgH(CO_3)_2$, $Ca(OH)_2$, $CaCO_3$, $Ca(HCO_3)_2$, CaO, $CH_6N_2O_2$, $C_2H_7N$ and mixtures thereof. Generally, the physical condition of the base can either be an aqueous solution, aqueous suspension, gaseous or solid.

In one embodiment the organic acid, in particular succinic acid, and/or salts thereof are produced by one of the above or below mentioned methods and are further isolated and/or purified by the following steps:
filtration and/or centrifugation,
cation exchange chromatography and/or
crystallization.

Preferably the organic acid and/or salts thereof are further isolated and/or purified by the following steps:
filtration, followed by
cation exchange chromatography, followed by
crystallization.

The filtration may be used to separate the bacterial cells from the succinic acid containing liquid. The filtration may be a diafiltration, crossflow-filtration and/or ultrafiltration.

The material used for cation exchange chromatography may be a strong acid cation exchange resin. A strong acid cation exchange resin carries for example sulfonic acid groups. In particular, the material used for cation exchange chromatography may be a styrol-divinyl benzol-copolymerisate carrying sulfonic acid groups in the H$^+$-form. H$^+$-form means that the sulfonic acid groups are present in the acid-form. Preferably, the average particle size of the cation exchange chromatography resin is 0.3 to 1.5, more preferably 0.55 to 0.75 mm and/or the bulk density is 700 to 800 g/l. The cation exchange chromatography resin may be macroporous. Makroporous means that preferably the average pore diameter of the cation exchange resin is from 20 to 120 nm, preferably from 20 to 100 nm and more preferably from 20 to 40 nm. The particle distribution is preferably monodispers. Preferably, the total capacity of the cation exchange chromatography material is 0.5 to 2.0, more preferably 0.8 to 1.7, more preferably 1.0 to 1.5, more preferably 1.4 to 1.9 min eq./l. x eq./l means that 1 l cation exchange resin carries x mol sulfonic acid groups. Accordingly eq./l is calculated with respect to a single charged molecule. The succinic acid salt to be purified may be a Na, K, Ca, Mg and/or ammonium salt. For example the strong acid cation exchange resin may be Type Lewatit Monoplus SP 112 from Lanxess.

Preferably, the cation exchange chromatography is performed at a temperature from 20 to 60° C., more preferably from 45 to 60° C.

Further preferred methods of producing SA are described below:
Method 1:
In another embodiment the present invention provides a process for the fermentative production of SA or a salt or derivative thereof, which process comprises the steps of:
a. incubating a bacterial strain in a medium containing at least one assimilatable carbon source and cultivating said strain under conditions favoring the formation of the desired organic acid;
b. obtaining said organic acid or salt or derivative thereof from the medium;
and which process is additionally characterized by conversion of at least 50 g/L of glycerol to at least 50 g/L SA, with a yield coefficient YP/S of at least 1.0 g/g, or of >1.0 g/g, or of >1.05 g/g, or of >1.1 g/g, or of >1.15 g/g, or of >1.20 g/g, or of >1.22 g/g, or of >1.24 g/g; up to about 1.28 g/g; as for example a yield coefficient YP/S of at least 0.6 g/g, of at least 0.7 g/g, of at least 0.75 g/g, of at least 0.8 g/g, of at least 0.85 g/g, of at least 0.9 g/g, of at least 0.95 g/g, of at least 1.0 g/g, of at least 1.05 g/g, of at least 1.1 g/g, of at least 1.15 g/g, of at least 1.20 g/g, of at least 1.22 g/g, or of at least 1.24 g/g. For example, 50 g/L of glycerol may be converted to up to about 65 or up to 62.5 g/L SA or up to 60 g/L SA.

Method 2:
In another embodiment the present invention provides a process for the fermentative production of SA or a salt or derivative thereof, which process comprises the steps of:
a. incubating a bacterial strain with a pyruvate-formate-lyase enzyme with decreased activity in a medium containing at least one assimilatable carbon source and cultivating said strain under conditions favoring the formation of the desired organic acid;
b. obtaining said organic acid or salt or derivative thereof from the medium;
and which process is additionally characterized by conversion of a carbon source selected from sucrose, maltose, maltodextrin, raffinose, D-fructose, D-glucose, D-xylose, L-arabinose, D-galactose, D-mannose, and/or glycerol to SA with a specific productivity yield of at least 0.42. g gDCW$^{-1}$ h$^{-1}$ SA or of at least of at least 0.45 or of at least 0.47 g g DCW$^{-1}$ h$^{-1}$ SA, or of at least 0.49 g gDCW$^{-1}$ h$^{-1}$ SA.

Method 3:
In another embodiment the present invention provides a process for the fermentative production of SA or a salt or derivative thereof, which process comprises the steps of:
a. incubating a bacterial strain with a pyruvate-formate-lyase enzyme with decreased activity in a medium containing at least one assimilatable carbon source and cultivating said strain under conditions favoring the formation of the desired organic acid;
b. obtaining said organic acid or salt or derivative thereof from the medium;
and which process is additionally characterized by conversion of a carbon source selected from sucrose, maltose, maltodextrin, raffinose, D-fructose, D-glucose, D-xylose, L-arabinose, D-galactose, D-mannose, and/or glycerol to SA with a space time yield for SA of at least 2.22 g/(L h), or of at least 2.5, at least 2.75, at least 2.9, g/(L*h) SA.

Method 4:
In another embodiment the present invention provides a process for the fermentative production of SA or a salt or derivative thereof, which process comprises the steps of:
a. incubating a bacterial strain in a medium containing at least one assimilable carbon source and cultivating said strain under conditions favoring the formation of the desired organic acid;
b. obtaining said organic acid or salt or derivative thereof from the medium;
and which process is additionally characterized by conversion of at least 50 g/L of a source selected from sucrose, maltose, maltodextrin, raffinose, D-fructose, D-glucose, D-xylose, L-arabinose, D-galactose, D-mannose, and/or glycerol to SA with a space-time-yield for SA of at least 2.2 g/(L h), or of at least 2.5, at least 2.75, at least 3, at least 3.25, at least 3.5 or at least 3.7 g/(L*h).

Method 5:
In another embodiment the present invention provides a process for the fermentative production of SA or a salt or derivative thereof, which process comprises the steps of:
a. incubating a bacterial strain in a medium containing at least one assimilatable carbon source and cultivating said strain under conditions favoring the formation of the desired organic acid;
b. obtaining said organic acid or salt or derivative thereof from the medium;
and which process is additionally characterized by conversion of a carbon source selected from sucrose, maltose, maltodextrin, raffinose, D-fructose, D-glucose, D-xylose, L-arabinose, D-galactose, D-mannose, and/or glycerol to SA with a specific productivity yield of at least 0.6 g gDCW$^{-1}$ h$^{-1}$ SA or of at least of at least 0.65 or of at least 0.7 g gDCW$^{-1}$ h$^{-1}$ SA, or of at least 0.75 g gDCW$^{-1}$ h$^{-1}$ SA, or of at least 0.77 g gDCW$^{-1}$ h$^{-1}$ SA and a space-time-yield for SA of at least of at least 2.2 g/(L h), or of at least 2.5, at least 2.75, at least 3, at least 3.25, at least 3.5 or at least 3.7 g/(L*h).

In another embodiment of the above identified methods 1 to 5 of producing SA the carbon source is glycerol or a mixture of glycerol and at least one further carbon source selected from sucrose, maltose, raffinose, maltodextrin, D-fructose, D-galactose, D-mannose, D-glucose, D-xylose, and L-arabinose.

Particularly suitable conditions for producing SA are:
Carbon source: Glucose, xylose, maltose or maltodextrin, raffinose and/or glycerol (including crude glycerol)
Temperature: 30 to 45° C.
pH: 5.5 to 7.0, controlled by a base as described above, preferably by a HCO$_3$ source such as Na$_2$CO$_3$, NaHCO$_3$, Mg(HCO$_3$)$_2$, Ca(HCO$_3$)$_2$ or, Mg(OH)$_2$, MgCO$_3$, Ca(OH)$_2$, CaCO$_3$.
supplied gas: CO$_2$ SA and/or SA salts produced may be isolated in conventional manner by methods known in the art, as for example crystallization, filtration, electrodialysis, chromatography. For example, they may be isolated by precipitating as a calcium succinate product in the fermentor during the fermentation by using calcium hydroxide, -oxide, -carbonate or hydrogencarbonate for neutralization and filtration of the precipitate. The desired SA product is recovered from the precipitated calcium succinate by acidification of the succinate with sulfuric acid followed by filtration to remove the calcium sulfate (gypsum) or which precipitates. The resulting solution may be further purified by means of ion exchange chromatography in order to remove undesired residual ions.

In another embodiment the present invention provides a process for the production of tetrahydrofuran (THF) and/or 1,4-butanediol (BDO) and/or gamma-butyrolactone (GBL), which comprises
b) the fermentative production of succinic acid and/or succinic acid salts, as defined above, and
b1) either the direct catalytic hydrogenation of the obtained free acid to THF and/or BDO and/or GBL or
b2) the chemical esterification of obtained free succinic acid and/or succinic acid salts to its corresponding di-lower-alkyl ester and subsequent catalytic hydrogenation of said ester to THF and/or BDO and/or GBL.

In another embodiment the present invention provides a process for the production of pyrrolidones which comprises
a) the fermentative production of succinic acid ammonium salts as defined above, and
b) the chemical conversion of succinic acid ammonium salts to pyrrolidones in a manner known per se.

In a particular embodiment of the processes of the said glycerol, which is used as assimilable carbon source, is crude glycerol, in particular obtained by ester cleavage of triacylglycerides. For example glycerol is a waste product as obtained from the manufacture of bio diesel.

The present invention also relates to the use of a bacterial strain as defined above for the fermentative production of an organic fine chemical, as for example succinic acid or a salt or derivative thereof.

d) Further Particular Embodiments d1) Genetic Manipulations

According to still another embodiment the bacterial strain of the invention contains a gene coding for a mutated enzyme of the pyruvate-formate-lyase (pfl) enzyme as its enzymatic activity is defined by the EC number EC 2.3.1.54. For example pfl enzyme activity is negatively influenced by the mutations in the pflA gene or by affecting the expressional regulation of the pflA gene. The sequence of the pflA gene and the pflA gene product can be found under the following accession numbers GeneID:6268899, YP_001880903: Homologues of this gene are known under the accession numbers: NCBI-GeneID 945514, 945444, 947623, 948454, 3075405, the respective proteins under the accession numbers: UniProt: P09373, P75793, P42632, P32674, Q65VK2.

Also within in the scope of this invention are genes coding for the pyruvate-formate-lyase activating enzymes which are defined by the EC number EC 1.97.1.4 and are described in Knappe et al. 1990 and 1993 with decreased or deregulated activity. This can be performed through introducing mutations or gene deletions by methods described in this invention. Examples for this enzyme which activities can be decreased or which coding gene can be mutated or deregulated are encoded by the pfl activating enzyme gene pflA and the yfiD gene, the *E. coli* K12 gene known under the accession GeneID: 947068, the gene ybiY, with the accession number NCBI-GeneID: 945445 and the respective protein NP_415345 the *Mannheimia succiniproducens* gene known under the accession GeneID: AAU37008, the respective proteins under the accession YP_087593, NP_417074 and YP_087564 as well as the homologues of this gene. Described are the accession numbers of the non-mutated gene sequences which are subject to mutations or deletions described in this invention.

Also in the scope of this invention are strains showing a reduced activity of the protein arcA eg. Accession: ECK4393 (also known under the following descriptions: cpxC, fexA, sfrA, msp) or fnr by carrying genetic mutations for the respective gene, known under the accession NCBI-GeneID: 948874 for arcA or NCBI-GeneID: 945908 for fnr. Respective protein sequences can be found under the Accession P0A9E5. Similar genes are known for other organisms such as *Mannheimia succinicproducens* namely. NCBI-GeneID: 3076294 and the respective protein YP_088696 for arcA and for fnr NCBI-GeneID:3075449 and UniProt: Q65TM6.

Also in the scope of this invention are strains showing a reduced activity of the lactate dehydrogenase defined by the EC number EC 1.1.1.27 and EC 1.1.1.28 coding for enzymes with a specificity of producing D-lactic or L-lactic acid or both. Examples are the *E. coli* genes NCBI-GeneID: 946315 and the respective protein NP_415898 or the *M. succiniproducens* gene NCBI-GeneID: 3075603 and the respective protein YP_089271.

According to still another embodiment the bacterial strain of the invention contains:

(1) a mutated gene coding for a pyruvate-formate-lyase enzyme defined by the EC nomenclature as EC 2.3.1.54, with decreased activity; and/or (2) a mutated gene coding for the pyruvate-formate-lyase activating enzyme defined by the EC nomenclature as EC 1.97.1.4 with decreased activity; and/or (3) a mutated gene coding for the arcA protein and/or (4) a mutated gene coding for a lactate dehydrogenase defined by the EC nomenclature as EC 1.1.1.27 or EC 1.1.1.28 with decreased activity.

A particular method for preparing genetically modified bacterial strains of the invention is a technique that is also sometimes referred to as the "Campbell recombination" herein (Leenhouts et al., 1989, Appl Env Microbiol 55, 394-400). "Campbell in", as used herein, refers to the preparation of a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out," as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert. The second recombination event results in the deletion (jettisoning) of a portion of the integrated DNA sequence, but, importantly, also results in a portion (this can be as little as a single base) of the integrated "Campbelled in" DNA remaining in the chromosome, such that compared to the original host cell, the "Campbell out" cell contains one or more intentional changes in the chromosome (for example, a deletion of the DNA sequence, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above).

A "Campbell out" cell is, preferably, obtained by a counter-selection against a gene that is contained in a portion (the portion that is desired to be jettisoned) of the "Campbelled in" DNA sequence, for example the *Bacillus subtilis* sacB gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, presence or absence of an enzymatic activity such as a pyruvate formate lyase activity or a lactate dehydrogenase activity, colony nucleic acid hybridization, antibody screening, etc. The term "Campbell in" and "Campbell out" can also be used as verbs in various tenses to refer to the method or process described above.

It is understood that the homologous recombination event that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

By applying the above method of genetic modification, mutant strains of a particular SA producer strain (i.e. DD1) were prepared by deleting the genes of endogenous pyruvate-formate-lyase enzyme and/or lactate dehydrogenase enzyme as described in more detail in the following examples.

d2) Fermentation Steps:

A fermentation as used according to the present invention can, for example, be performed in stirred fermentors, bubble columns and loop reactors. A comprehensive overview of the possible method types including stirrer types and geometric designs can be found in "Chmiel: Bioprozesstechnik: Einführung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Before the intended chemical conversion in a fermentation broth is performed in the process according to the invention, the fermentation broth can be pretreated; for example, the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value. In one embodiment, the fermentation broth can be sterilized or pasteurized.

In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

Stirred tanks, falling-film evaporators, thin-film evaporators, forced-flash circulation evaporators and other evaporator types can be utilized in natural or forced circulation mode.

d3) Esterification of SA and Hydrogenation:

Suitable experimental conditions for performing the chemical esterification, followed by direct catalytic hydrogenation are well known, and for example, described in European Patent application 06007118.0 incorporated herewith by reference.

a) Esterification Process:

The esterification process, which may comprise a reactive distillation can be performed using an apparatus known per se in various designs.

For example an esterification plant, which is operated in continuous mode can be used which comprises a rectification column with an appropriate number of theoretical stages achieved by installation of trays or packings. The aqueous charge comprising the ammonium salt of SA is fed into the top of the column from a reservoir vessel as soon as a steady-state temperature profile has formed in the column as a result of feeding-in alkanol that is evaporated in the evaporator loop adherent to the sump of the column. The reaction forms a countercurrent flow of descending, ammonium salt-containing liquid and condensate, and ascending, alkanol-containing vapor phase. To catalyze the esterification reaction, a homogeneous catalyst may be added to the ammonium salt initial charge. Alternatively, heterogeneous catalysts may be provided in the column internals. The carboxylic ester formed is liquid under the process conditions and passes via the lower end of the column into the sump of the distillation column and is continuously withdrawn from the sump. Gaseous components, for example azeotropic mixtures comprising alkanol-water and/or ammonia, are removed from the reaction column and hence from the reaction equilibrium at the top of the column.

Further modifications of the above-described specific embodiments can be implemented by the person skilled in the art without unacceptable effort.

Suitable process parameter ranges for the esterification process according to the invention can be determined easily by the person skilled in the art depending on the configuration of the apparatus used, for example type of column internals used, type and amount of the reactants, type and amount of the catalyst used if appropriate. For instance, without being restrictive thereto, individual parameters may be set within the following parameter ranges:

Column temperature: 0-300° C., in particular 40-250° C., or 70-200° C.

Pressure: from 0.1 to 6 bar, in particular standard pressure

Residence time: a few seconds (for example from 1 to 60) up to days (for example from 1 to 5), in particular from a few minutes (for example from 1 to 60) to a few hours (for example from 1 to 15), more preferably from a few minutes (for example from 5 to 20) to 2 h.

b) Hydrogenation Process

The SA esters or SA as prepared in accordance with the invention per se are hydrogenated in a manner known per se using processes, apparatus and assistants, such as catalysts, familiar to the person skilled in the art.

In particular, a continuous or batchwise gas phase hydrogenation is carried out in the presence of a heterogeneous catalyst suitable for the ester hydrogenation. The optimal process parameters can be established by the person skilled in the art for the particular ester without unacceptable effort. For example, the reaction temperature is in the range from about 100 to about 300° C., preferably in the range from about 200 to about 280° C., and the pressure is from about 5 to 100 bar, for example from 10 to 50 bar. The molar ratio of reactant to hydrogen is set within the range from about 1:100 to about 1:2000, for example from 1:800 to 1:1500.

Catalysts usable for the hydrogenation reaction are known to the person skilled in the art. For example, various copper catalysts may be used. The prior art describes, for example, the use of reduced copper chromite catalysts which are obtainable under the name 85/1 from Davy Process Technology Ltd., England. However, catalysts particularly suitable in accordance with the invention are supported copper oxide catalysts, the copper oxide being applied to alumina or silica support materials. The examples of the hydrogenation of succinic esters to BDO (1,4-Butanediol)/GBL (gamma-butyrlactone)/THF with copper catalysts are also described in the following thesis: Schlander, January, February 2000, University of Karlsruhe, "Gasphasenhydrierung von Maleinsäuredimethylester zu 1,4-Butandiol, gamma-Butyrolacton and Tetrahydrofuran an Kupfer-Katalysatoren".

The present invention will be described in greater detail by means of the following examples. The following examples are for illustrative purposes and are not intended to limit the scope of the invention.

EXAMPLES—GENETIC MODIFICATION AND CULTIVATION

Example 1: General Method for the Transformation of DD1

TABLE 1

Nomenclature of the DD1 wildtype and mutants referred to in the examples.

| Strain | Description |
|---|---|
| LU13843 | Wildtype DD1 (deposit DSM18541) |
| LU15348 | DD1 Δ pfl |
| LU15050 | DD1 Δ ldh |
| LU15224 | DD1 Δ pfl Δ ldh |

*Pasteurella* strain LU13843 (wildtype DD1) was transformed with DNA by electroporation using the following protocol:

For preparing a pre-culture LU 13843 was inoculated from a freshly grown BHI-Agar plate into 40 ml BHI (brain heart infusion, Difco) in 100 ml shake flask. Incubation was performed over night at 30° C.; 200 rpm.

For preparing the main-culture 50 ml BHI were placed in a 100 ml shake flask and inoculated to a final OD (610 nm) of 0.4 with the preculture. Incubation was performed for approximately 1.5 h at 30° C., 200 rpm. The cells were harvested at an OD of approximately 1.3, pellet were washed once with 10% cold glycerol at 4° C. and resuspended in 1.7 ml 10% glycerol (4° C.).

100 µl of competent cells were the mixed with 5-10 µg DNA (10-20 µl) and kept on ice for 2 min in an electroporation cuvette with a width of 0.2 cm. Electroporation under the following conditions: 800Ω; 25 µF; 2 kV (Gene Pulser, Bio-Rad). 1 ml of BHI was added immediately after electroporation. and an incubation was performed for 2 h at 30° C.

Cells were plated on BHI with 5 mg/L chloramphenicol and incubated for 2-5 d at 30° C. until the colonies of the transformants were visible. Clones were isolated and restreaked onto BHI with 5 mg/l chloramphenicol until purity of clones was obtained.

Example 2: Generation of Deletion Constructs

Figure 2:
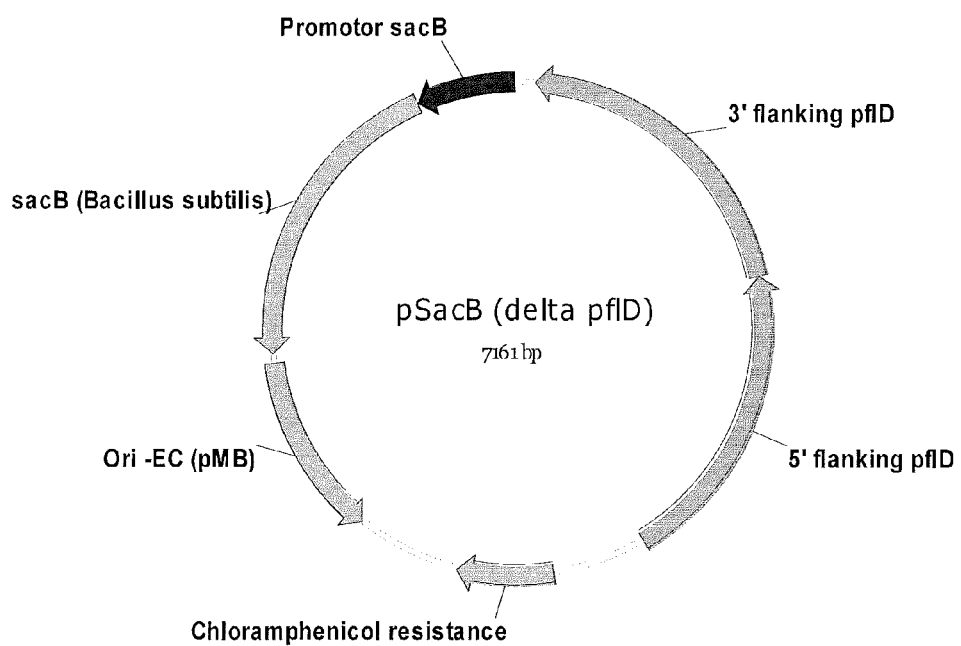
FIG. 2 depicts a schematic map of plasmid pSacB (delta pfl) (SEQ ID NO:4).
Figure 3:
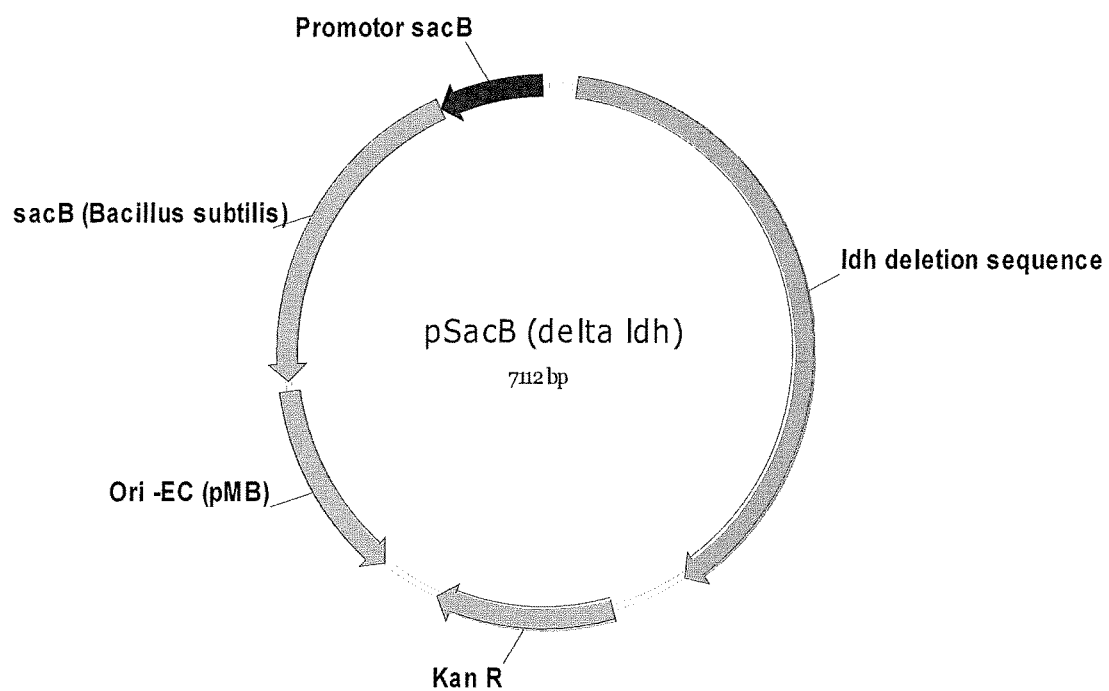
FIG. 3 depicts a schematic map of plasmid pSacB (delta ldh) (SEQ ID NO:5).

Mutation/deletion plasmids were constructed based on the vector pSacB (SEQ ID NO 3). FIG. 1 shows a schematic map of plasmid pSacB. 5'- and 3'-flanking regions of the chromosomal fragment, which should be deleted were amplified by PCR from chromosomal DNA of LU 13843 and introduced into said vector using standard techniques. Normally, at least 80% of the ORF were targeted for a deletion. In such a way, the deletion plasmids for the pyruvate-formate-lyase pfl, pSacB (Δpfl), (SEQ ID NO 4), and the lactate dehydrogenase ldhA, pSacB (ΔldhA) (SEQ ID NO 5) were constructed. FIGS. 2 and 3 show schematic maps of plasmid pSacB (Δpfl) and pSacB (ΔldhA).

In the plasmid sequence of pSacB (SEQ ID NO:3) the sacB gene is contained from bases 5169-6590. The chloramphenicol gene is contained from base 526-984. The sacB promotor is contained from bases 3802-4264. The chloramphenicol gene is contained from base 526-984. The origin of replication for *E. coli* (ori EC) is contained from base 1477-2337.

In the plasmid sequence of pSacB delta pfl (SEQ ID NO:4) the 3' flanking region of the pfl gene, which is homologous to the genome of DD1, is contained from bases 65-1533, while the 5' flanking region of the pfl gene which is homologous to the genome of DD1 is contained from bases 1534-2956. The sacB gene is contained from bases 5256-6677. The sacB promoter is contained from bases 6678-7140. The chloramphenicol gene is contained from base 3402-3860. The origin of replication for *E. coli* (ori EC) is contained from base 4353-5213.

In the plasmid pSacB delta ldh (SEQ ID NO:5) the 5' flanking region of the ldh gene, which is homologous to the genome of DD1, is contained from bases 2850-1519, while the 3' flanking region of the ldh gene, which is homologous to the genome of DD1, is contained from bases 1518-63. The sacB gene is contained from bases 5169-6590. The sacB promoter is contained from bases 6591-7053. The chloramphenicol gene is contained from base 3315-3773. The origin of replication for *E. coli* (ori EC) is contained from base 4266-5126.

Example 3: Generation of Improved Succinate Producing Strains a) LU 13843 was transformed as described above with the pSacB (Δpfl) and "Campbelled in" to yield a "Campbell in" strain. Transformation and integration into the genome of LU 13843 was confirmed by PCR yielding bands for the integrational event of the plasmid into the genome of LU 13843.

The "Campbell in" strain was then "Campbelled out" using agar plates containing sucrose as a counter selection medium, selecting for the loss (of function) of the sacB gene. Therefore, the "Campbell in" strains were incubated in 25-35 ml of non selective medium (BHI containing no antibiotic) at 37° C., 220 rpm over night. The overnight culture was then streaked onto freshly prepared BHI containing sucrose plates (10%, no antibiotics) and incubated overnight at 37° C. ("first sucrose transfer"). Single colony obtained from first transfer were again streaked onto freshly prepared BHI containing sucrose plates (10%) and incubated overnight at 37° C. ("second sucrose transfer"). This procedure was repeated until a minimal completion of five transfers ("third, forth, fifth sucrose transfer") in sucrose. The term "first to fifth sucrose transfer" refers to the transfer of a strain after chromosomal integration of a vector containing a sacB levansucrase gene onto sucrose and growth medium containing agar plates for the purpose of selecting for strains with the loss of the sacB gene and the surrounding plasmid sequences. Single colony from the fifth transfer plates were inoculated onto 25-35 ml of non selective medium (BHI containing no antibiotic) and incubated at 37° C., 220 rpm over night. The overnight culture was serially diluted and plated onto BHI plates to obtain isolated single colonies.

The "Campbelled out" strains containing the mutation/deletion of the pfl gene were confirmed by chloramphenicol sensitivity. The mutation/deletion mutants among these strains were identified and confirmed by PCR analysis. This led to the pfl mutation/deletion mutant DD1 delta pfl LU 15348.

b) LU15348 was transformed with pSacB (Δldh) as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the pfl ldhA double deletion mutant LU15224.

c) LU 13843 was transformed with pSacB (Δldh) as described above and "Campbelled in" to yield a "Campbell in" strain. Transformation and integration was confirmed by PCR. The "Campbell in" strain was then "Campbelled out" as described previously. The deletion mutants among these strains were identified and confirmed by PCR analysis. This led to the ldhA deletion mutant LU15050.

Example 4: Cell Bank Preparation

1. Media Preparation

Composition of the cultivation media is described in table 2.

TABLE 2

Composition of solid and liquid media for the preparation of cell banks.

| Compound | Concentration [g/l] | Concentration of stock solution [g/l] |
|---|---|---|
| Glucose | varying$^a$ | 650 |
| Bacto yeast extrakt (Becton Dickinson) | 5 | — |
| Bacto peptone (Becton Dickinson) | 5 | — |
| (NH4)$_2$ SO$_4$ | 1 | 500 |
| CaCl$_2$*2H$_2$O | 0.2 | 20 |
| MgCl$_2$*6H$_2$O | 0.2 | 20 |
| NaCl | 1 | 100 |
| K$_2$HPO$_4$ | 3 | 500 |
| MgCO$_3$ | Varying$^b$ | — |
| Bacto-Agar (for solid media only) | 12 | |

$^a$Glucose concentrations were 15 g/l (in plates) and 20 or 50 g/l (in liquid media).
$^b$MgCO$_3$ (Riedel-de Haen, product number: 13117 by Sigma-Aldrich Laborchemikalien GmbH) concentrations were 5 g/l (in plates) and 0 or 30 g/l (in liquid media).

5 g yeast extract, 5 g peptone, MgCO$_3$ and (for solid media) 12 g Bacto-Agar were mixed in 900 ml distilled water and autoclaved (20 min). After cooling down to about 65° C. the missing components were added as sterile stock solutions. Glucose, ammonium sulfate and K$_2$HPO$_4$ were all separately autoclaved. Ca-, Mg- and Na-chlorides were autoclaved together.

2. MCB Preparation

The master cell bank (MCB) for the inoculation of the individual experiments was performed as followed. Two agar plates were freshly inoculated with the desired strain and incubated at 37° C. in an anaerobic jar (Anaerocult A, Merck) over night. The biomass was taken off the plates and resuspended in the MgCO$_3$-free liquid medium with 20 g/l glucose to adjust OD$_{600}$≈1.0. Inoculation was performed with 0.5 ml of this cell suspension. Cultivations were performed in 100 ml-serum bottles with gas tight butyl rubber stoppers (Ochs GmbH, Bovenden/Lenglern, Germany) containing 50 ml of the liquid medium with 20 g/l glucose and 30 g/l MgCO$_3$ and a CO$_2$— atmosphere with 0.8 bar overpressure. The serum bottles (in total 10) were incubated at 37° C., a rotary speed of 160 rpm and a shaking diameter of 2.5 cm.

To monitor glucose consumption the cultivation of one bottle was stopped and sampling and HPLC analysis were performed after 0, 3, 4, 5, 7, 8 and 8.5 h. After 8.5 h (the glucose concentration was 3.4 g/l) the cultivation was stopped. Aliquots of 0.5 ml cell suspension and 0.5 ml sterile glycerol were filled in cryovials, mixed and stored for 13 h at −20 and afterwards at −80° C. as MCB. The MCB was tested for purity by streaking a loop of the last cryovial on agar plates for contamination control and checking in liquid culture (media as described table 8) the product spectrum and for contamination (by microscopy).

Consumption of glucose and formation of SA and by-products were quantified via HPLC analyses of the undiluted cell free supernatants of the cultivation broth using RI-detection. Broth samples were taken with a sterile syringe through the butyl rubber plug, cell separation was performed by filtration (0.22 µm). A 300×7.8 mm I. D. Column Aminex HPX-87 H (Biorad) and 5 mm H2SO4 were used as stationary and mobile phase, respectively. The column temperature was 30° C., the flow rate was 0.5 ml min$^{-1}$.

One vial of the MCB was used to inoculate a 100 ml-serum bottle with gas tight butyl rubber stopper (see above) containing 50 ml of the liquid medium with 50 g/l glucose. Incubation was performed for 10 h at 37° C. in a shaking incubator (rotary speed: 180 rpm, shaking diameter: 2.5 cm). At the end of the cultivation the glucose concentration was 20 g/l and the pH around 6.5. Aliquots of 0.5 ml cell suspension and 0.5 ml sterile glycerol were filled in cryovials, mixed and stored at −80° C. as WCB. Purity checks were the same as for the MCB. HPLC conditions were the same as those described above.

Example 5: Cultivation of Various DD1 Strains on Glycerol or Glycerol and Maltose The productivity of the mutant strain DD1Δpfl (LU15348) and DD1Δpflαldh (LU15224) in the presence of gylcerol or glycerol and maltose as a carbon source was further analyzed utilizing the following medium and incubation conditions.

1. Medium Preparation

The composition and preparation of the cultivation medium is as described in the following table 3.

TABLE 3

Medium composition for DD1 cultivation on the substrates glycerol or glycerol and maltose.

| | Compound | Concentration [g/l] |
|---|---|---|
| 1 | Bacto yeast extrakt (Becton Dickinson) | 10 |
| 2 | (NH$_4$)$_2$SO$_4$ | 2 |
| 3 | CaCl$_2$*2H$_2$O | 0.2 |
| 4 | MgCl$_2$*6H$_2$O | 0.2 |
| 5 | NaCl | 1 |
| 6 | K$_2$HPO$_4$ | 3 |
| 7 | MgCO$_3$ (Riedel-de Haen 13117) | 1 g/g substrate |
| 9 | NaHCO$_3$ | 8.4 |
| 10 | substrate | varying |

Alternative Synthetic Growth Medium

It is favorable to use a synthetic growth medium without complex ingredients for the fermentation in order to improve downstream processing and design a synthetic growth medium for cost efficient fermentation.

Medium Preparation

The synthetic growth medium was developed in relation to other synthetic growth media for rumen bacteria (Nili and Brooker, 1995, McKinlay et al, 2005), previous in house experience with other bacteria and by performing single omission experiments. Finally, the medium contained 50 g/L glucose, 1 g/L $(NH_4)_2SO_4$, 0.2 g/L $CaCl_2*2H_2O$, 0.2 g/L $MgCl_2*6H_2O$, 1 g/L NaCl, 3 g/L $K_2HPO_4$, 1 mg/L nicotinic acid, 1.5 mg/L pantothenic acid, 5 mg/L pyridoxine, 5 mg/L riboflavin, 5 mg/L biotin, 1.5 mg/L thiamin HCl, 0.26 g/L lysine, 0.15 g/L threonine, 0.05 g/L methionine, 0.71 g/L glutamic acid, 0.06 g/L histidine, 0.07 g/L tryptophane, 0.13 g/L phenylalanine, 0.06 g/L tyrosine, 0.5 g/L serine, 0.5 g/L glycine, 0.5 g/L cysteine, 0.1 g/L β-Alanine, 0.27 g/L alanine, 0.19 g/L valine, 0.23 g/L leucine, 0.16 g/L isoleucine, 0.33 g/L aspartic acid, 0.1 g/L asparagine, 0.13 g/L proline, 0.15 g/L arginine and/or 0.1 g/L glutamine.

Serum bottles containing 50 mL of synthetic growth medium were autoclaved with water and 30 g/L $MgCO_3$ as the buffer system. Glucose, ammonium sulfate and potassium phosphate were sterilized, separately. Ca-, Mg- and Na-chlorides were sterilized together. Vitamins and amino acids were assembled in various stock solutions and filter sterilized. After cooling down the serum bottles the components were added as sterile stock solutions.

2. Cultivations and Analytics

For growing the seed culture one vial of the WCB was used to inoculate a 100 ml-serum bottle with gas tight butyl rubber stopper (see above) containing 50 ml of the liquid medium described in table 2 but with 20 g/l glucose and a $CO_2$— atmosphere with 0.8 bar overpressure. Incubation was performed for a mutant-specific number of hours (table 4) at 37° C. and 160 rpm (shaking diameter: 2.5 cm) The cell suspension was centrifuged (Biofuge primo R, Heraeus,) with 5000 g for 5 minutes and the cell pellet was washed and then resuspended in 50 ml medium without a carbon source and without $MgCO_3$ to generate a glucose-free inoculum (all steps at room temperature and in the anaerobic chamber).

TABLE 4

Incubation time of various DD1 mutant seed cultures

| Strain | Hours of incubation |
| --- | --- |
| LU 13843 | 8 hrs |
| LU 15050 | 10 hrs |
| LU 15348 | 13 hrs |
| LU 15228 | 20 hrs |

The main cultures were grown in 100 ml-serum bottles containing 10 ml liquid medium with either 50 g/l glycerol or 50 g/l glycerol and 10 g/l D-maltose and in both cases a $CO_2$— atmosphere with 0.8 bar overpressure. The quality 'Glycerol 99%, puriss.' (Riedel-de Haen, product number: 15523-1 L-R by Sigma-Aldrich Laborchemikalien GmbH, Seelze, Germany) was used for all experiments. Inoculation was performed with 1.5 ml of the glucose-free inoculum. The bottles were incubated at 37° C., and 160 rpm (shaking diameter: 2.5 cm).

Consumption of the C-sources and production of carboxylic acids was quantified via HPLC as described in example 4 after 24 h. As glycerol was measured the column temperature was adjusted to 50° C. to achieve a sufficient separation of SA, lactic acid and glycerol which have similar retention times.

Cell growth was measured by measuring the absorbance at 660 nm ($OD_{600}$) using a spectrophotometer (Ultrospec3000, Amersham Biosciences, Uppsala Sweden). Cell concentration defined as gram dry cell weight (DCW) per liter was calculated from the pre-determined standard curve relating the $OD_{600}$ to DCW (1 $OD_{600}$=0.27 g DCW $l^{-1}$).

3. Results

The results of the cultivation experiments with for different DD1 strains are shown in table 5 for the substrate glycerol and table 6 for the substrate mixture of glycerol and maltose.

TABLE 5

Cultivation of various DD1 strains on glycerol

| DD1 strain | LU13843 | LU15348 | LU15050 | LU15224 |
| --- | --- | --- | --- | --- |
| tc [h]$^a$ | 24 | 24 | 24 | 24 |
| $\Delta c_{Glycerol}$ [g/l]$^b$ | −17.3 | −25.8 | −17.4 | −28.6 |
| $\Delta c_{SA}$ [g/L]$^c$ | 19.5 | 29.9 | 19.9 | 36.2 |
| $\Delta c_{LA}$ [g/L]$^{c,h}$ | <0.01 | <0.01 | <0.01 | 0.04 |
| $\Delta c_{FA}$ [g/l]$^{c,h}$ | 0.2 | 0.05 | 0.2 | <0.01 |
| $\Delta c_{AA}$ [g/l]$^{c,h}$ | 1.0 | 0.6 | 1.1 | 0.3 |
| $\Delta c_{PA}$ [g/l]$^{c,h}$ | 0.3 | <0.01 | 0.4 | <0.01 |
| $\Delta c_{MA}$ [g/l]$^{c,h}$ | <0.01 | <0.01 | <0.01 | <0.01 |
| Sum of side products SSP [g/l]$^d$ | 1.5 | 0.7 | 1.7 | 0.3 |
| SA/SSP [g/g]$^e$ | 13.0 | 46.0 | 11.7 | >100 |
| Ratio SA/FA$^f$ | 97.5 | >100 | 99.5 | >100 |
| Ratio SA/AA$^f$ | 19.5 | 49.8 | 18.1 | >100 |
| STY [g/(l h)]$^g$ | 0.81 | 1.24 | 0.82 | 1.50 |
| Carbon Yield (YP/S) [g/g ]$^g$ | 1.12 | 1.15 | 1.13 | 1.26 |

$^a$cultivation time.
$^b$consumption of substrate (glycerol, maltose).
$^c$formation of succinic, lactic, formic, acetic, pyruvic and malic acid.
$^d$sum of side products lactic, formic, acetic, pyruvic and malic acid.
$^e$ratio of SA per sum of side products.
$^f$ratio of SA per side product (FA = formic acid; AA = acetic acid).
$^g$space time yield and yield (YP/S) for SA.
$^h$Detection limits for acetic acid, lactic acid, malic acid, and formic acid were found to be lower than 0.01 g/l in the given HPLC method In the glycerol-cultivation experiment it is shown that knocking out the pyruvate format lyase gene pfl in a SA producing organism as e.g. DD1 leads to significantly higher carbon yield (YP/S) and STY for SA as for the wildtype when grown on glycerol as a substrate. The carbon yield (YP/S) is increased from 1.12 g/g for the DD1 strain to 1.15 g/g for the Δ pfl mutant strain LU 15348.

Other than reported by Lee et al, 2006 or Lin et al 2005 for SA producing bacteria on glucose, knocking out only the lactate dehydrogenase gene ldhA in DD1 (LU15050) shows no improvement of the technical relevant characteristics of this fermentation such as STY of SA and only minor increase in carbon yield (YP/S). The amount of acetic acid however is even increased if the lactate dehydrogenase enzyme activity is decreased. Surprisingly and unexpectedly from the analysis of the behavior of strains with the single mutations it was found that the mutant strain carrying the combination of the gene mutations in the pfl and the ldh gene the fermentation of glycerol to SA shows even larger non additive improvement to the reached carbon yield (YP/S) as was expected from the single mutations of LU 15050 and LU15348. The carbon yield (YP/S) of 1.26 g/g observed is close to the potential theoretical carbon yield (YP/S) of 1.28 g/g for the conversion of 1 Mol glycerol+1 Mol $CO_2$ to 1 Mol of SA.

Also the sum of side products (SSP) generated in LU15348 is significantly decreased while growing on glycerol as no formic acid and less acetic acid is produced. As mentioned above, the SA concentration is significantly increased compared to wildtype or LU15050. This observation is expressed in the ratios of SA over the arithmetic sum of side products (SSP) SA:SSP g/g, which exceeds 40 for LU15348 and exceeds 100 for LU15224 compared to a level of 10 for LU13843 and LU15050.

In the aforementioned experiment it was found that the STY of fermentation of glycerol to SA did not exceed 1.5 g/(l*h) for strains carrying mutations in the pfl and ldh genes. Therefore, an improved process was developed that showed improved STY values for the production of SA in an anaerobic fermentation. This process is described in the application PCT/EP2008/006714 on the pages 44-46. This process was adapted for the production of succinate utilizing strains carrying mutations in the genes.

TABLE 6

Cultivation of various DD1 strains on glycerol and maltose

| | LU13843 | LU15348 | LU15050 | LU15224 |
|---|---|---|---|---|
| tc [h]$^a$ | 24 | 24 | 24 | 24 |
| $\Delta c_{Glycerol}$ [g/L]$^b$ | −41.2 | −48.2 | −40 | −51.3 |
| $\Delta c_{Maltose}$ [g/L]$^b$ | −11.5 | −10.9 | −11.3 | −11.3 |
| $\Delta c_{SA}$ [g/L]$^c$ | 53.2 | 64.7 | 51.8 | 69.8 |
| $\Delta c_{LA}$ [g/L]$^{c,i}$ | <0.01 | 2.5 | <0.01 | 0.1 |
| $\Delta c_{FA}$ [g/L]$^{c,i}$ | 2.8 | <0.01 | 3.0 | <0.01 |
| $\Delta c_{AA}$ [g/L]$^c$ | 3.8 | 0.7 | 3.6 | 1.5 |
| $\Delta c_{PA}$ [g/L]$^{c,i}$ | <0.01 | 0.6 | 0.1 | 0.4 |
| $\Delta c_{MA}$ [g/L]$^{c,i}$ | 0.05 | 0.03 | 0.03 | 0.1 |
| Σ SP [g/L]$^d$ | 6.65 | 3.8 | 6.73 | 2.1 |
| SA/SSP [g/g]$^e$ | 8.0 | 16.9 | 7.7 | 33.2 |
| Ratio SA/FA$^f$ | 19.11 | >100 | 17.1 | >100 |
| Ratio SA/AA$^f$ | 13.9 | 92.7 | 14.2 | 46.2 |
| STY [g/(L h)]$^g$ | 2.21 | 2.69 | 2.15 | 2.90 |
| Yield (YP/S) [g/g]$^g$ | 1.01 | 1.09 | 1.01 | 1.11 |
| $OD_{600}$$^h$ | 12.9 | 14.8 | 16.4 | 18.6 |
| DCW [g/L]$^i$ | 3.5 | 4 | 4.4 | 5 |
| Specific productivity [g gDCW$^{-1}$ h$^{-1}$]$^k$ | 0.63 | 0.67 | 0.49 | 0.58 |

$^a$cultivation time.
$^b$consumption of substrate (glycerol, maltose).
$^c$formation of succinic, lactic, formic, acetic, pyruvic and malic acid.
$^d$sum of side products lactic, formic, acetic, pyruvic and malic acid.
$^e$ratio of SA per sum of side products.
$^f$ratio of SA per side product (FA = formic acid; AA = acetic acid).
$^g$space time yield and yield (YP/S) for SA.
$^h$Optical density at 600 nm, diluting the sample 1:20 with 1M HCl before measuring in a Ultrospec2000, Amersham Biosciences, Uppsala Sweden.
$^i$g Biomass as dry cell weight (DCW)
$^h$Specific productivity: g SA per g biomass (dry cell weight) per h
$^i$Detection limits for acetic acid, lactic acid, malic acid and formic acid were found to be lower than 0.01 g/l in the given HPLC method Growing DD1 on glycerol simultaneously with another saccharide maltose has been shown to allow for a higher SA STY and yield (YP/S) and an increased concentration of side products as compared to using glycerol as the sole substrate (PCT/EP2008/006714 on the pages 44-46).

Comparing LU15348 to the DD1 wildtype shows increased SA amount, STY and carbon yield (YP/S) if the activity of the Pfl enzyme is decreased. Surprisingly, in contrast to other examples described in the state of the art (Lee et al 2006, Lin et al 2005), no growth defect was observed in the mutant strains over the non-mutated strain DD1. This observation is of great technical relevance since good growth of a strain is essential for a technical production process. Cell growth is increased in all mutants compared to the wildtype. Knocking out either pfl or ldh has a positive effect on growth of the mutated bacterial strain.

Due to lack of detectable formic acid, decreased amount of acetic acid and increased SA concentration, the ratio SA/SSP is increased in mutant strains containing decreased enzyme activity of Pfl inferred by genetic mutations. However, the side product lactic acid has increased compared to the wildtype. The double knockout LU15224 has a further increased yield (YP/S) and STY while LU15050 did not show any improvement in carbon yield (YP/S), STY or the SSP observed.

It is noted that the pfl mutation is necessary and sufficient to improve the fermentation of glycerol with and without a second saccharide substrate over the performance of a wildtype strain in a SA process based on the metabolization of glycerol. In contrast to this finding a prior art pfl mutation in a wildtype derived strain has not been shown to induce the fermentation of SA (Zhu 2005). Only the combinations of several mutations including pfl and ldh did result in a measurable succinic acid production albeit at reduced growth and poor STY performance (Lin 2005, Lee 2006). The finding of this work teaches the construction of an improved process for the fermentative production of SA consisting of a mutated strain together with a specific process to yield a process with superior performance over the prior art.

Surprisingly, the specific productivity for SA is superior for the pfl mutant strain LU15348 over LU15050 and LU15224 carrying mutations in the ldh gene and in both ldh and pfl genes. It is known to the expert in the field that depending on the process a high specific activity of product formation is a desirable characteristic of a technical process. Obviously, the negative effect of knocking out lactate dehydrogenase lowers the specific productivity of LU15348 below the value of the wildtype.

Example 6: Cultivation of LU15348 on Mixtures of Glycerol with Various Carbohydrates The productivity of the mutant strain LU15348 in the presence of glycerol and various carbohydrates as a carbon source was analyzed utilizing the following medium and incubation conditions.

1. Medium Preparation, Cultivation and Analytics

The composition and preparation of the cultivation medium is as described in the table 3 of example 5. Cultivation and analytics occur as described in example 5.

The quality 'Maltodextrin' (Maldex150, Cat. no.: 50499 by Boom, 7942 JE Meppel, The Netherlands) was used within this experiment. Due to the undefined mixture of saccharide chains with various lengths the concentration of maltodextrin was not analyzed to full extent by HPLC-analytics. Therefore, maltodextrin content was determined gravimetrically precisely before being added to the cultivation medium. In order to calculate the lower limit of the achieved theoretical yield (YP/S) it was assumed that all the maltodextrin added to the fermentation had been consumed, being aware that this will allow only for calculation of the lower limit of carbon yield (YP/S) after SA fermentation. More likely, the more exact values of the carbon yield (YP/S) will be higher than the described values due to potentially incomplete consumption of the substrate maltodextrin which is undetected.

2. Results

The results of the cultivation experiments for LU15348 are shown in table 7 for the substrate glycerol in cofermentation with various carbohydrates as e.g. maltose, maltodextrin or raffinose.

TABLE 7

Cultivation of LU15348 on glycerol in cofermentation with various carbohydrates

| LU15348 | Glycerol + 10 g/L Maltose | Glycerol + 10 g/L Maltodextrin | Glycerol + 17 g/L Raffinose | Glycerol |
|---|---|---|---|---|
| tc [h]$^a$ | 24 | 24 | 24 | 24 |
| $\Delta c_{Glycerol}$ [g/L]$^b$ | −48.2 | −30.5 | −37.4 | −25.8 |
| $\Delta c_{Carbohydrate}$ [g/L]$^b$ | −10.9 | n.a. | −1.5 | — |
| $\Delta c_{SA}$ [g/L]$^c$ | 64.7 | 48.4 | 35.6 | 29.9 |
| $\Delta c_{LA}$ [g/L]$^c$ | 2.5 | 1.0 | 0.2 | <0.01 |
| $\Delta c_{FA}$ [g/L]$^{c,i}$ | <0.01 | <0.01 | <0.01 | 0.05 |
| $\Delta c_{AA}$ [g/L]$^c$ | 0.7 | 0.4 | 0.3 | 0.6 |
| $\Delta c_{PA}$ [g/L]$^{c,i}$ | 0.6 | <0.01 | 0.2 | <0.01 |
| $\Delta c_{MA}$ [g/L]$^{c,i}$ | 0.03 | <0.01 | <0.01 | <0.01 |
| Σ SP [g/L]$^d$ | 3.8 | 0.4 | 0.5 | 0.7 |
| Ratio SA/SSP [g/g]$^e$ | 16.9 | >100 | 71.2 | 46.0 |
| Ratio SA/FA$^f$ | >100 | >100 | >100 | >100 |
| Ratio SA/AA$^f$ | 92.7 | >100 | >100 | 49.8 |
| STY [g/(L h)]$^g$ | 2.69 | 2.02 | 1.48 | 1.24 |
| Yield (YP/S) [g/g]$^g$ | 1.09 | ≥1.02* | 1.11 | 1.15 |

$^a$cultivation time.
$^b$consumption of substrate (glycerol, maltose).
$^c$formation of succinic, lactic, formic, acetic, pyruvic and malic acid.
$^d$sum of side products lactic, formic, acetic, pyruvic and malic acid.
$^e$ratio of SA per sum of side products.
$^f$ratio of SA per side product (FA = formic acid; AA = acetic acid).
$^g$space time yield and yield (YP/S) for SA.
$^i$Detection limits for acetic acid, lactic acid, malic acid and formic acid were found to be lower than 0.01 g/l in the given HPLC method
*lower limit of yield (YP/S) due to unknown residual maltodextrin concentration which was not analyzed.

Cultivating strain LU15348 on glycerol in cofermentation with diverse saccharides such as maltose, a mixture of high molecular saccharide such as maltodextrin or still another saccharide raffinose, leads to similar results showing that the simultaneous fermentation of diverse carbon sources including glycerol as one carbon source leads to a number of technically relevant improvements of SA production over the state of the art previously described. Examples are increased rates and improved total amounts of glycerol consumed by the process, leading to higher SA titers as compared to the state of the art. Additionally, the STY is increased over the control not containing a saccharide. Side product concentration is generally diminished, except in the case of maltose as cosubstrate, where lactic acid is the increased side product compared with the sole glycerol cultivation. The SA yield (YP/S) is similar or only slightly diminished compared to glycerol as the only substrate.

Summary of the Experiments
  microorganisms that have decreased pfl activity show improved fermentation on glycerol over the state of art
  combinations of different carbon sources are efficiently converted into succinic acid
  microorganisms that have decreased pfl activity show improved fermentation on a mixture of glycerol and a saccharide over the state of art Conclusion:
  The new process for the production of succinic acid (SA) has an excellent potential for the production of SA and/or SA salts, with carbon high yield (YP/S) and space time yield as well as very low side products.

In the context of the present invention a bacterial strain DD1 (ID 06-614) was deposited with DSMZ (Deutsche Sammlung von Mikroorganismen und Zellkulturen GmbH, Inhoffenstr. 7B, D-38124 Braunschweig, Germany) on Aug. 11, 2006 having the deposit number DSM 18541. In this context reference is made to the priority European patent application No. EP 09152959.4 and EP 09171250.5, wherein the deposit was mentioned the first time within the context of the present invention. Furthermore, reference is made to WO 2009/024294, wherein the DD1 strain is described the first time including the deposition at DSMZ (Deutsche Sammlung von Mikroorganismen und Zellkulturen GmbH, Inhoffenstr. 7B, D-38124 Braunschweig, Germany) on Aug. 11, 2006.

The content of the documents cited herein is incorporated by reference.

Examples—Downstream Processing

Example 7: Method for Isolation of Succinic Acid from Fermentation Broths by Cation Ion Exchange Resin A fermentation broth neutralized by NH$_4$OH (25 weight.-%, calculated on the total weight of the NH$_4$OH-solution) during the fermentation process was filtrated. The aqueous, cell free fermentation broth containing 15% (w/w) succinic acid (neutralized as salt) was used for the downstream process.

A cation exchange resin (type Lewatit Monoplus SP 112 from Lanxess; 471 ml) was filled in a temperature controlled (50° C.) glass column (bed elevation: 24 cm) as stationary phase and washed with water. After this washing step the resin was overflowed in a top down way with the aqueous succinic acid solution (156 ml, containing 25 g succinic acid, density: 1.069 kg/l). The flow velocity of the solution averaged 33 ml/min corresponding to a velocity of 4.2 bed volumes (BV) per hour.

Thus a clear and uncolored solution containing approximately 24.9 g free succinic acid was obtained in the first fraction (453 ml). The succinic acid concentration of this fraction averaged 5.38 weight.-%.

Beside the index of refraction the pH value and the adsorption (350 nm) of the solution coming out of the column were measured.

The resulting binding capacity of the used strong acid cationic exchanger resin averaged approximately 0.89 equivalents (eq) per liter resin.

After the binding process the resin was washed with water (546 ml) and finally regenerated in the cationic form with 5% hydrochloric acid (919 ml; velocity: 66 ml/min) which overflowed the resin bottom up. As a last step the resin was washed again with water (889 ml).

In addition to the fact, that the resin released the succinic acid, the resin decolorized the broth and a very pure and colorless succinic acid solution was obtained.

Example 8: Method for Measuring a Break Through Curve with a Strong Acid Ion Exchange Resin Aqueous, cell free fermentation broth containing an amount of 15% (w/w) succinic acid (neutralized as salt) was used for the downstream process after filtration.

A strong acid ion exchange resin (type Lewatit MonoPlus SP 112 from Lanxess; 689 ml) was filled in a temperature controlled (50° C.) glass column (bed elevation: 97.5 cm) and washed with water. After this washing step the resin was overflowed in a top down way with the aqueous succinic acid solution (468 ml, containing 75 g succinic acid; density: 1.069 kg/l). The flow velocity of the solution averaged 24 ml/min corresponding to a velocity of 2.1 bed volumes (BV) per hour.

As in example 7, a clear solution (457 ml) containing approximately 53.8 g free succinic acid was obtained in the first fraction. The succinic acid concentration of this fraction averaged 11.53 weight-%.

Unlike the assay in example 7, in this case the sampling of the first fraction was stopped at the moment the cations broke trough. This moment was detected with the measured pH value which increased suddenly (from an approximately value of 1.4) due to breaking through succinic acid salt.

The sampled fraction after this clear solution contained succinic acid salt and has a brown color similar to the original fermentation broth.

In this assay the resulting binding capacity of the used strong acid cationic exchanger resin averaged approximately 1.32 equivalents (eq) per liter resin.

After the binding process the resin was washed with water (678 ml) and regenerated in the cationic form with 5% hydrochloric acid (2034 ml; velocity: 92 ml/min). Finally the resin was washed again with water (824 ml).

In addition to the fact, that the resin released the succinic acid, the resin decolorized the broth and a very pure and colorless succinic acid solution was obtained.

Example 9: Method for Purifying Succinic Acid from Fermentation Broths Followed by Concentration and Crystallization of the Resulting Desalted Solution Two samples were used for the crystallization step and gained in the same way as described in example 7.

In each case aqueous, cell free fermentation broth containing an amount of 15% (w/w) succinic acid (neutralized as salt) was used for the downstream process. The two samples which were purified and desalted by using a cationic exchange resin (type Lewatit MonoPlus SP 112 from Lanxess) were used for the crystallization step.

The following tables show the volume of fermentation broth, resin and chemicals plus the obtained quantities and capacities in these trials.

| Trial number | Fermenta- tion broth | resin | Dosing velocity | fraction 1 | Succinic acid concentration in fraction 1 |
|---|---|---|---|---|---|
| 34649-069 | 249 ml | 471 ml | 33 ml/min | 462 ml | 8.43% |
| 34649-098 | 249 ml | 471 ml | 53 ml/min | 517 ml | 7.57% |

| Trial number | Succinic acid in fraction 1 | Washing water after binding | HCl (5%) for resin regeneration | Washing water after regenera- tion | Resulting binding capacity |
|---|---|---|---|---|---|
| 34649-069 | 39.7 g | 481 ml | 919 ml | 928 ml | 1.43 eq/l |
| 34649-098 | 39.9 g | 526 ml | 919 ml | 730 ml | 1.44 eq/l |

Thus two clear and uncolored solutions were obtained as first fractions and combined to gain one succinic solution (with approximately 76 g free succinic acid; difference due to the sampling).

This solution was concentrated by distilling off water to gain 380.2 g solution with a succinic acid concentration of 20 weight-%. After the concentration step, the solution was stirred and cooled down. Once the solution had a temperature of 50° C., it was seeded. Shortly after, the crystallization began and succinic acid crystals precipitated.

The succinic acid suspension was stirred over night at ambient temperature and cooled down in an ice/water bath for 1 hour.

The crystals were filtered off in the cold and the cake was washed two times with 20 ml ice water each. After the washing step the crystals were dried in a nitrogen gas flow. Thus 65.2 g colorless succinic acid crystals with a purity of 99.8% were obtained.

Subsequently, the succinic acid crystals were dried in a fluid be dryer.

REFERENCES

Botstein, D, Shortie, D (1985) Strategies and applications of in vitro mutagenesis. Science 229 1193-201

Dharmadi Y, Murarka A, Gonzalez R (2006) Anaerobic fermentation of glycerol by *Escherichia coli*: A new platform for metabolic engineering. Biotech Bioeng 94: 821-829.

Dousse et al. (2008) Routine phenotypic identification of bacterial species of the family Pasteurellaceae isolated from animals Dousse, Fjournal of veterinary diagnostic investigation 20 716-724

Eisenstark, A (1971) Mutagenic and lethal effects of visible and near-ultraviolet light on bacterial cells. Adv Genet 16 167-98

Hong S H, Lee S Y (2001) Metabolic Flux analysis for SA production by recombinant *Escherichia coli* with amplified malic enzyme activity. Biotechnology and Bioengineering 74/2: 89-95.

Foster, Patricia L, (2007) Stress-induced mutagenesis in bacteria. Crit Rev Biochem Mol Biol 42 373-97

Knappe, J, et al. (1993) Pyruvate formate-lyase mechanism involving the protein-based glycyl radical. Biochem Soc Trans 21 731-4

Knappe, J, Sawers, G (1990) A radical-chemical route to acetyl-CoA: the anaerobically induced pyruvate formate-lyase system of *Escherichia coli*. FEMS Microbiol Rev 6 383-98

Kuhnert, P. and Christensen, H. 2008 "Pasteurellaceae: Biology, Genomics and Molecular Aspects."; ISBN 978-1-904455-34-9.

Kuhnert P, Scholten E, Haefner S, Mayor D and Frey J (2010), *Basfia succiniproducens* gen. nov., sp. nov., A new member of the family Pasteurellaceae isolated from bovine rumen (2010) International Journal of Systematic and Evolutionary Microbiology, 60, 44-50.

Lee P C, Lee S Y, Hong S A, Chang H N (2002a) Isolation and characterization of a new SA-producing bacterium, *Mannheimia succiniciproducens* MBEL 55E, from bovine rumen. Appl Microbiol Biotechnol 58: 663-668.

Lee S J, Song H, Lee S Y (2006) Genome-Based Metabolic engineering of *Mannheimia succiniciproducens* for SA production. Appl Environ Biotechnol 72/3: 1939-1948.

Leenhouts et al., 1989, Appl Env Microbiol 55, 394-400

Lin H, San K-Y, Bennett G N (2005) Effect of *Sorghum vulgare* phosphoenolpyruvate carboxylase and *Lactococcus lactis* pyruvate carboxylase coexpression on succinate production in mutant strains of *Escherichia coli*. Appl Microbiol Biotechnol 67: 515-523.

Pascal, M et al. (1981) Mutants of *escherichia-coli-k12* with defects in anaerobic pyruvate metabolism Journal of General Microbiology 124 35-42

Peters-Wendisch, P G et al. (1996) Archives of Microbiology 165 387-396.

Peters-Wendisch P G, (1998). Microbiology. 144, 915-27.

Saier, Milton H Jr (2008) The bacterial chromosome Crit Rev Biochem Mol Biol 43 89-134

Sambrook et al., (1989) MOLECULAR CLONING: A LABORATORY MANUAL, Second Edition, Cold Spring Harbor Laboratory, Cold Spring Harbor, N.Y. ["Sambrook"].

Sanchez A M, Bennet G N, San K-Y (2005) Novel pathway engineering design of the anaerobic central metabolic pathway in *Escherichia coli* to increase succinate yield and productivity. Metabolic Engineering 7: 229-239.

Sawers, G (1993): specific transcriptional requirements for positive regulation of the anaerobically inducible pfl operon by arca and fnr molecular microbiology 10 737-747

Song H and Lee S (2006) Production of SA by bacterial fermentation. Enz Microb Tech 39: 352-361.

Varenne s et al. (1975) Mutant of *escherichia-coli* deficient in pyruvate formate lyase, molecular & general genetics 141 181-184

Walker, G C (1984) Mutagenesis and inducible responses to deoxyribonucleic acid damage in *Escherichia coli*. Microbiol Rev 48 60-93

Walker, G C et al. (1983) Regulation and function of cellular gene products involved in UV and chemical mutagenesis in *E. coli*. Basic Life Sci 23 181-202

Witkin, E M (1969) Ultraviolet-induced mutation and DNA repair. Annu Rev Microbiol 23 487-514

Yazdani S, Gonzalez R (2007) Anaerobic fermentation of glycerol: a path to economic viability for the biofuels industry. Curr Opinion Biotechnol 18: 213-219.

Zhu, et al. (2005) Effect of a single-gene knockout on the metabolic regulation in *Escherichia coli* for D-lactate production under microaerobic condition Metab Eng 7 104-15

The invention claimed is:

1. A bacterial strain, capable of utilizing glycerol as a carbon source for the fermentative production of succinic acid, wherein said strain is genetically modified so that it comprises a deregulation of its endogenous pyruvate-formate-lyase enzyme activity, and wherein said pyruvate-formate-lyase enzyme activity is decreased or switched-off, and wherein the strain is derived from a microorganism of the family of Pasteurellaceae, and comprises the 16S rDNA sequence of SEQ ID NO: 1 or a sequence having at least 96% sequence homology to SEQ ID NO: 1.

2. The strain of claim 1, wherein at least one further enzyme activity involved in or associated with the fermentative conversion of glycerol to succinate is deregulated.

3. The strain of claim 1, derived from a microorganism of the family of Pasteurellaceae, and comprising the 23S rDNA sequence of SEQ ID NO: 2 or a sequence having at least 95% sequence homology to SEQ ID NO: 2.

4. The strain of claim 1, showing at least one of the following additional metabolic characteristics:
   a) production of succinic acid from sucrose;
   b) production of succinic acid from maltose;
   c) production of succinic acid from maltodextrin;

d) production of succinic acid from D-fructose;
e) production of succinic acid from D-galactose;
f) production of succinic acid from D-mannose;
g) production of succinic acid from D-glucose;
h) production of succinic acid from D-xylose;
i) production of succinic acid from L-arabinose;
j) production of succinic acid from lactose;
k) production of succinic acid from raffinose;
l) production of succinic acid from glycerol;
m) growth at an initial glucose concentration of 75 g/L or more; or
n) growth at an initial glycerol concentration of 70 g/L or more.

5. The strain of claim 1 which converts sucrose, maltose, D-fructose, D-glucose, D-xylose, L-arabinose, D-galactose, lactose, D-mannose, raffinose and/or glycerol to succinic acid with a yield coefficient YP/S of at least 0.5 g/g.

6. The strain of claim 1, having at least one of the following characteristics
a) converting at least 25 g/L of glycerol to at least 25.1 g/L succinic acid, with a yield coefficient YP/S of at least 1.01 g/g;
b) converting at least one carbon source selected from sucrose, maltose, maltodextrin, D-fructose, D-glucose, D-xylose, L-arabinose, D-galactose, lactose, D-mannose, raffinose, and/or glycerol to succinic acid with a specific productivity yield of at least 0.58 g gDCW-1 h-1 succinic acid;
c) converting at least one carbon source selected from sucrose, maltose, D-fructose, D-glucose, D-xylose, L-arabinose, D-galactose, lactose, D-mannose, and/or glycerol to succinic acid with a space time yield for succinic acid of at least 2.2 g/(L h) succinic acid;
d) converting at least 25 g/L of at least one carbon source selected from sucrose, maltose, D-fructose, D-glucose, D-xylose, L-arabinose, D-galactose, lactose, D-mannose, and/or glycerol to succinic acid with a space-time-yield for succinic acid of at least 2.2 g/(L h); or
e) converting at least one carbon source selected from sucrose, maltose, maltodextrin, D-fructose, D-glucose, D-xylose, L-arabinose, D-galactose, lactose, D-mannose, raffinose, and/or glycerol to succinic acid with a specific productivity yield of at least 0.58 g gDCW-1 h-1 succinic acid and a space-time-yield for succinic acid of at least 2.2 g/(L h).

7. The strain of claim 1, which produces succinic acid (SA) and side products (SSP) in an SA/SSP proportion of >10:1, or >12.5:1, or >15:1, or >17.5.1, or >20:1, or >25:1, or >30:1, or >33:1, wherein SSP represents the sum of side products lactic acid (LA), formic acid (FA), acetic acid (AA), and malic acid (MA), each amount being expressed in g/L.

8. The strain of claim 1, which produces succinic acid (SA) and the side product acetic acid (AA) in an SA/AA proportion of >10:1, or >12.5:1, or >15:1, or >17.5:1, or >20:1, or >25:1, or >30:1, or >40:1 or >50:1, or >75:1, or >90:1, each amount being expressed in g/L.

9. The strain of claim 1, which produces succinic acid (SA) and the side product formic acid (FA) in an SA/FA proportion of >90:1, or >100:1, each amount being expressed in g/L.

* * * * *